(12) United States Patent
Han et al.

(10) Patent No.: US 11,053,189 B2
(45) Date of Patent: Jul. 6, 2021

(54) METHOD AND MIXTURE TO FORM FUNCTIONALIZED CYCLIC COMPOUNDS

(71) Applicant: National Tsing Hua University, Hsinchu (TW)

(72) Inventors: Chien-Chung Han, Hsinchu (TW); Suman Alishetty, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 16/362,709

(22) Filed: Mar. 25, 2019

(65) Prior Publication Data

US 2020/0308101 A1  Oct. 1, 2020

(51) Int. Cl.
 *C07D 307/68* (2006.01)
 *C07C 231/14* (2006.01)
 (Continued)

(52) U.S. Cl.
 CPC .......... *C07C 231/14* (2013.01); *C07C 233/57* (2013.01); *C07C 249/04* (2013.01); *C07C 253/02* (2013.01); *C07D 307/68* (2013.01)

(58) Field of Classification Search
 CPC ... C07C 231/14; C07C 253/02; C07C 233/57; C07C 249/04; C07D 307/68
 (Continued)

(56) References Cited

U.S. PATENT DOCUMENTS 7,745,439 B2  6/2010 Cheon et al.

FOREIGN PATENT DOCUMENTS

| CN | 101851177 | 10/2010 |
|---|---|---|
| WO | 2004041161 | 5/2004 |
| WO | 2005100303 | 10/2005 |

OTHER PUBLICATIONS

Suman Alishetty et al., "One-Step, Effective, and Cascade Syntheses of Highly Functionalized Cyclopentenes with High Diastereoselectivity," Org. Lett., vol. 20, Issue 9, Apr. 17, 2018, pp. 2513-2516.
(Continued)

*Primary Examiner* — Taylor V Oh
(74) *Attorney, Agent, or Firm* — JCIPRNET

(57) ABSTRACT

A method for producing a homocyclic or heterocyclic compound includes reacting a compound of formula (I) with a compound of formula (II) in presence of a base:

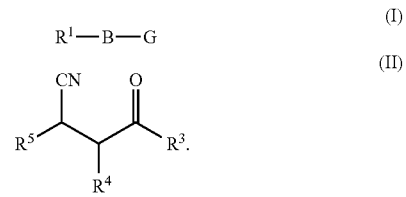

In formula (I), B is an unsaturated moiety selected from substituted or unsubstituted vinylene, ethynylene, aryleneethynylene, substituted or unsubstituted arylenevinylene, and a combination thereof, the vinylene or arylenevinylene has n (=0, 1 or 2) substituent(s) $R^2$, G is an electron-withdrawing group, $R^1$ is hydrogen or a substituent, and two of $R^1$, $R^2$ and G may joint together to form a ring. In formula (II), $R^3$ and $R^4$ are independently hydrogen or a substituent, $R^5$ is an electron-withdrawing group, and two of $R^3$, $R^4$ and $R^5$ may joint together to form a ring. The conjugate acid of the base has a $pK_a$ in the range of 1 to 15.

11 Claims, 8 Drawing Sheets

(III-1)

(51) Int. Cl.
*C07C 253/02* (2006.01)
*C07C 249/04* (2006.01)
*C07C 233/57* (2006.01)

(58) Field of Classification Search
USPC .................................................. 549/474
See application file for complete search history.

(56) References Cited

OTHER PUBLICATIONS

Mandy K. S. Vink et al., "Nitrile hydrolysis activity of Rhodococcus erythropolis NCIMB 11540 whole cells," Biotechnol. J., vol. 1, Issue 5, May 2006, pp. 569-573.
Gao et al., "Nitrile hydrolysis activity of Rhodococcus erythropolis NCIMB 11540 whole cells," ChemCatChem, vol. 8, Issue 22, Nov. 22, 2016, pp. 3466-3474.
Daniel T. Ziegler et al., "Biphenyl-Derived Phosphepines as Chiral Nucleophilic Catalysts: Enantioselective [4+] Annulations to Form Functionalized Cyclopentenes," Angew. Chem. Int. Ed., vol. 53, Issue 48, Nov. 24, 2014, pp. 13183-13187.
Saleh M. Al-Mousawi et al., "Polyfunctional Nitriles in Organic Syntheses: A Novel Route to Aminopyrroles, Pyridazines and Pyrazolo[3,4-c]pyridazines," Molecules, vol. 14, Issue 2, Feb. 16, 2019, pp. 798-806.
Fathy M. Abdelrazek et al., "Phenacyl Bromides Revisited: Facile Synthesis of Some New Pyrazoles, Pyridazines, and Their Fused Derivatives," Journal of Heterocyclic Chemistry, vol. 51, Issue 2, Mar. 2014, pp. 475-481.
Jose M. Rodriguez et al., "Straightforward synthesis of nitroolefins by microwaveor ultrasound-assisted Henry reaction," Tetrahedron Letters, vol. 52, Issue 21, May 25, 2011, pp. 2629-2632.
S. Ahadi et al., "Diastereoselective synthesis of polysubstituted cyclopentanols and cyclopentenes containing stereogenic centers via domino Michael/cyclization reaction," Tetrahedron, vol. 71, Issue 38, Sep. 23, 2015, pp. 6860-6866.
Lingchao Cai et al., "Chemoselective phosphine-catalyzed cascade annulations between two different activated alkenes: highly diastereoselective syntheses of polysubstituted cyclohexanes and cyclopentenesw," Chem. Commun., vol. 47, Nov. 15, 2011, pp. 1045-1047.

(III-1)

(III-16)

(X-2)

(IV-3)

METHOD AND MIXTURE TO FORM FUNCTIONALIZED CYCLIC COMPOUNDS

BACKGROUND OF THE INVENTION

Field of Invention

This invention relates to functionalized organic compounds and their preparation, and more particularly relates to a method for forming highly functionalized cyclic compounds (e.g., cyclopentenes, and cyclopentadiene oximes).

Description of Related Art

A great variety of medicinal or bioactive compounds present a functionalized cyclopentene moiety within their structure. For example, a functionalized cyclopentene core having a quaternary allylic carbon bearing a carboxamide group and an electron-withdrawing group is a structural motif of tetrahydropyranal cyclopentyl benzylamide (TCB) compounds. TCB have been shown to regulate the activity of chemokine receptors, and their use has been suggested in the treatment of diseases or conditions associated with inflammations or infections (cf. Butora et al., WO 2004/041161 A2). Similarly, compounds presenting a functionalized cyclopentadienone-oximes moiety have shown modulator activity for peroxisome proliferated activated receptors (PPAR, cf. Cheon et al., WO 2005/100303 A1).

Currently available synthetic routes towards functionalized cyclopentene or cyclopentadienone-oxime derivatives tend to be unsatisfactory as involving numerous reaction steps, using expensive catalysts or reagents, and being applicable for only limited substrate scope. For example, Vink et al. (*Biotechnol. J.*, 2006, 1, 569) obtained functionalized cyclopentene derivatives including a quaternary carbon center bearing a carboxamide group and another electron withdrawing group from malononitrile via double α-allylation, ring-closure metathesis and enzyme-differentiated hydrolysis. Products including a similar core were obtained starting from a cyanoesteramide by Gao et al. (*ChemCatChem*, 2016, 8, 3466), via double α-allylation and ring-closure metathesis, or by Ziegler et al. (*Angew. Chem. Int. Ed.*, 2014, 53, 13183) via a phosphine-catalyzed [4+1] annulation with an asymmetric allenoate. In all the aforementioned cases, the stereogenic quaternary carbon is in the 1-position to the vinyl group, rather than in the desirable allylic position. Concerning the cyclopentadienone oxime moieties, these have been chiefly prepared by reaction of hydroxylamine with cyclopentadienones, which might require several steps to be prepared (cf., in the case of indenones, Cheon et al., U.S. Pat. No. 7,745,439 B2).

In light of the interesting biological activity displayed, there is a great need of more straightforward routes towards functionalized cyclopentenes and cyclopentadienone oxime derivatives. As at least in the case of cyclopentenes derivatives where the formation of new stereogenic centres is involved, reaction routes that produces predominantly a specific pair of diastereoisomer would be, in general, preferred.

SUMMARY OF THE INVENTION

Accordingly, this invention provides an effective, low-cost, environmentally friendly method for forming functionalized unsaturated homocyclic or heterocyclic compounds, such as cyclohexenes, cyclopentenes or cyclopentadienone oximes derivatives.

This invention also provides an effective, low-cost, environmentally friendly method for forming functionalized cyclopentadienone oximes derivatives starting from functionalized cyclopentenes.

This invention further provides a reaction mixture to form functionalized cyclopentenes or cyclopentadienone oximes.

This reaction is based on the effectiveness of mild bases to act as dual functional organocatalysts to promote a cascade Michael reaction between a Michael acceptor and a dual functional compound that contains both a Michael donor moiety and a less reactive Michael acceptor moiety to form a cyclic compound.

In a method to produce a homocyclic or heterocyclic compound, a compound of formula (I) is reacted with a compound of formula (II) in presence of a base.

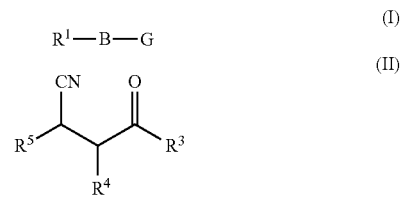

In formula (I), B is an unsaturated moiety, selected from the group consisting of substituted or unsubstituted vinylene, ethynylene, aryleneethynylene, substituted or unsubstituted arylenevinylene, and a combination thereof, such as vinylene-ethynylene (e.g., an enyne moiety), diene, triene, tetraene, polyene, diacetylene, triacetylene, arylene-vinylene, vinylene-arylene-vinylene, arylene-ethynylene, ethynylene-arylene-ethynylene, and ethylene-arylene-ethynylene. The vinylene or arylenevinylene has n substituent(s) $R^2$, wherein n is 0, 1 or 2, and when n is 2, the two $R^2$ may be the same or different, and may joint together to form a ring. G is an electron-withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, electron-withdrawing heteroaromatic groups, halogen-substituted alkyl groups, and halogen atoms.

$R^1$ is hydrogen or a substituent, and may joint together with $R^2$ to form a ring. Likewise, either $R^1$ or $R^2$ may joint together with G to form a ring. In formula (II), each of $R^3$ and $R^4$ is independently hydrogen or a substituent, and $R^3$ and $R^4$ are the same or different. $R^5$ is an electron-withdrawing group comprising the permissible group of G. Two of $R^3$, $R^4$ and $R^5$ may joint together to form a ring. In some embodiments, the conjugate acid of the base has a $pK_a$ in the range from 1 to 15.

The inventor has found out that the reaction might proceed with higher diastereoselectivity when the base is a mild base that can promote coordination between the proton on the activated methylene of the compound of formula (II) and the carbonyl group of the same compound. In some derivative methods of this invention, the base comprises a fluoride-containing ion. In some other derivative method, the base is an organic fluoride salt such as a tetraalkylammonium fluoride compound.

Without being bound to or limited by any chemical theory, it is possible that the base promotes the reaction by hydrogen-bonding to the most acidic and positively charged hydrogen of the compound of formula (II), namely the hydrogen bonded to the activated methylene being attached to the cyano and $R^5$ groups. It might be envisioned that the H-bonding interaction between the base and the activated methylenic proton polarizes the C—H bond, thus increasing the ionization degree and the acidity of the proton. The proton might then be able to coordinate the oxygen of the carbonyl group moiety, forming a transient five-membered ring adduct (VII).

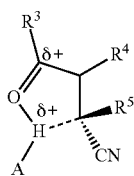

(VII)

In formula (VII), A represents the base or a constituent thereof used within the reaction, for example a fluoride anion.

In some methods according to this invention, the reaction is carried out in a solvent. In some embodiments of this invention, the solvent is an aprotic solvent that is lacking of N—H or O—H protons, so that solvation interaction between the base and the solvent can be avoided. In some alternative embodiments of this invention, the solvent has a dielectric constant of at least 6, to better polarize the C—H bond of the activated methylene carbon in the compound of formula (II). In some alternative embodiments, an anhydrous solvent is used, to prevent solvation interaction of water impurities with the base.

In some embodiments, the reaction is stirred at a temperature in a range from 0° C. to 45° C.

In some embodiments, a product of the reaction of the compound of formula (I) with the compound of formula (II) is a cyclopentene compound of formula (III).

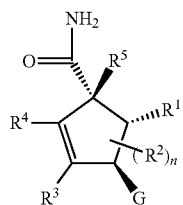

(III)

In formula (III), G, n, $R^1$, $R^2$, $R^3$, $R^4$, and $R^5$ are the same as in formulae (I) and (II).

In some embodiments, the cyclopentadiene compound of formula (III) is obtained as a racemic mixture.

Without being bound to or limited by any chemical theory or mechanistic proposal, it is possible that the activated methylene carbon in the adduct (VII) can act as a nucleophilic center, whilst the carbonyl group is an activated electrophilic center. Adduct (VII) might rapidly undergo a sequence of two Michael reactions with a compound of formula (I) to form a cyclic compound of formula (VIII).

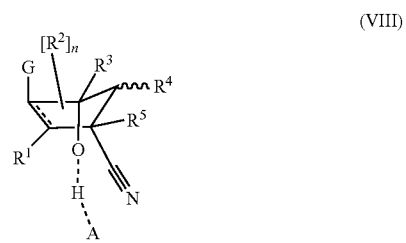

(VIII)

In formula (VIII), G, $R^1$, $R^2$, $R^3$, $R^4$, $R^5$ and n can be the same substituents or assume the same values as in compounds of formulae (I) and (II). The dashed line indicates that the corresponding bond can be a single or a double bond.

Upon formation of the cyclic compound (VIII) the relative stereochemistry of the substituents $R^1$ and G is fixed. When B in formula (I) is a trans double bond, the cyclic compound (VIII) is a cyclopentanol, and $R^1$ and G maintain their trans relationship within the cycle. It is possible that in the conditions disclosed by the present invention the two-steps reaction between the compound of formula (I) and the compound of formula (II) is fast enough or even concerted, leading to a retention of the stereochemistry of the compound of formula (I) in the compounds of formulae (VIII) and (III).

When the bond corresponding to the dashed bond in formula (VIII) indicates a single bond, the cyclic compound (VIII) might evolve by hydrolysis of the cyano group and elimination of the hydroxyl substituent to form a cyclopentene derivative of formula (III). It is possible that the hydroxylic group formed from the carbonyl group of compound (II) interacts with the cyano group in cis to the same hydroxyl group, for example through protonation or hydrogen bonding interaction, thereby activating the cyano group towards a nucleophilic attack of the hydroxyl oxygen to form a bicyclic compound (IX). It can be envisioned that the base might promote the proton transfer or the hydrogen bonding interaction by acting as an intermediary.

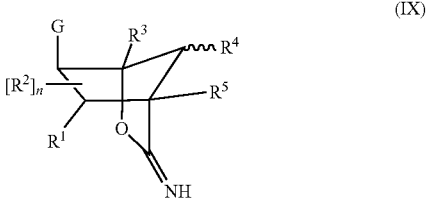

(IX)

In formula (IX), G, $R^1$, $R^2$, $R^3$, $R^4$, $R^5$ and n can be the same substituents or assume the same values as in compounds of formulae (I) and (II).

The imino nitrogen of the compound of formula (IX) might be activated through protonation yielding the corresponding cation, which might evolve through base-assisted elimination (E2) or unimolecular elimination (E1) to form a cyclopentene compound of formula (III). Without being limited to or bound by any chemical theory or mechanistic hypothesis, a transfer of the hydroxyl group to the cyano group in cis configuration in the cyclic compound (VIII) might explain the observed diastereoselectivity in the compound of formula (III).

In some embodiments, a diastereoisomer of formula (III-B) is also formed during the reaction.

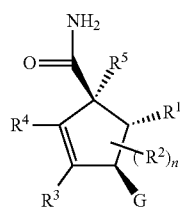

(IIIB)

The compound of formula (III-B) is an epimer of the compound of formula (III) at the allylic quaternary carbon. In some embodiments of the present invention, the reaction produces larger amounts of the compound of formula (III) than its epimer (III-B). The compound (III) and the epimer (III-B) are formed as a racemic mixture in absence of chiral induction.

In some embodiments, a cyclopentadiene compound of formula (III), in which G is $NO_2$, $R^4$ is H, and n is 0 or 1, may be further reacted to obtain a compound of formula (IV).

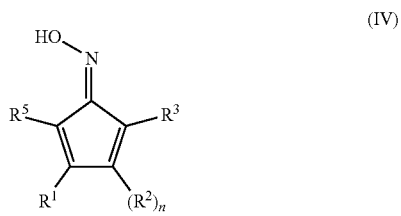

(IV)

In formula (IV), each of $R^1$, $R^2$, $R^3$, $R^5$, and n are the same as in the corresponding compound of formula (III). In some embodiments, the compound of formula (III) is isolated from the reaction mixture before being reacted to form the compound of formula (IV). In some alternative embodiments, the reaction may be carried to directly obtain the compound of formula (IV) skipping the purification step of the compound of formula (III). As a non-limiting example, once it is decided that formation of the compound of formula (III) is completed or that the reaction has progressed enough, the reaction mixture might be subjected to the condition of formation of the compound of formula (IV) without any intermediate purification step. In some embodiments, compound (IV) may be obtained directly from the reaction mixture of compounds (I) and (II) by performing the reaction directly at effective elevated temperatures.

In some alternative method of this invention, a compound of formula (V) is obtained by reacting a compound of formula (VI).

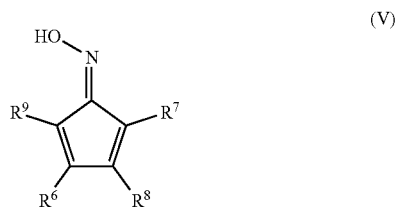

(V)

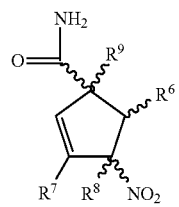

(VI)

In formula (V) and in formula (VI), each of $R^6$, $R^7$ and $R^8$ is independently a hydrogen or a substituent, $R^6$, $R^7$, and $R^8$ are the same or different. $R^9$ is hydrogen, a substituent selected from the permissible groups of $R^6$, $R^7$ and $R^8$, or an electron withdrawing group selected from the aforementioned permissible groups of G. Either $R^9$ and $R^6$, or $R^9$ and $R^7$, or $R^9$ and $R^8$ may joint together to form a ring.

In some embodiments of the present disclosure, the compound of formula (VI) is reacted at a temperature in a range between 50° C. and 140° C.

In some alternative embodiments, the compound of formula (VI) is reacted in presence of a base, and a conjugated acid of the base has a $pK_a$ in the range of 1 to 15, more preferably in the range of 1 to 13.5. In some embodiments, the base comprises a fluoride-containing ion. In some embodiments, the molar ratio of the base to the compound of formula (VI) is in the range of 0.001 to 10, more preferably in the range of 0.001 to 0.5.

According to some embodiments of the present invention, a reaction mixture is provided comprising a compound of formula (I), a compound of formula (II), and a base.

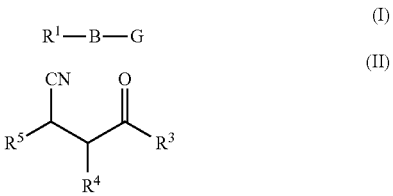

Formula (I) and (II) are as defined above. The conjugate acid of the base has a $pK_a$ in the range of 1 to 15, more preferably in the range of 1 to 13.5.

In some embodiments, the reaction might proceed with higher diastereoselectivity when the base is a mild base that can promote coordination between the proton on the activated methylene of the compound of formula (II) and the carbonyl group of the same compound of formula (II). In some reaction mixtures according to the present invention, the base comprises a fluoride-containing ion. In some reaction mixtures, the base is an organic fluoride salt, such as a tetraalkylammonium fluoride compound.

A reaction mixture according to some embodiments of the present invention may include an aprotic solvent. In some alternative embodiments, the solvent may have a dielectric constant of at least 6. In some alternative embodiments, the solvent may be anhydrous.

A reaction mixture according to some embodiments of the present disclosure may include a compound of formula (VI) and a base.

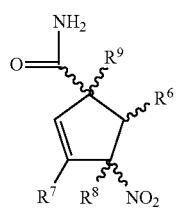

(VI)

Formula (VI) is as defined above. The conjugated acid of the base has a $pK_a$ in the range from 1 to 15, more preferably in a range of 1 to 13.5.

In some embodiments, the base in the reaction mixture comprises a fluoride-containing ion.

In some embodiments, the molar ratio of the base to the compound of formula (VI) is in the range of 0.001 to 10, more preferably in a range of 0.001 to 0.5.

Because the disclosed method does not use air- and moisture-sensitive reagents, the required chemical handling is relatively easy. Moreover, since the method needs a simple production facility and the manufacturing process is simple and safe, the manufacturing cost is low. In addition, since at least part of the reaction can be effectively conducted at ambient temperature, the method is also energy-saving. Also, the manufacturing process of the method of this invention is heavy-metal free, so that the method is environmentally friendly.

In order to make the aforementioned and other objects, features and advantages of this invention comprehensible, a preferred embodiment accompanied with figures is described in detail below.

It should be noted that although mechanistic hypotheses concerning the path followed by the reaction are presented, such discussions are provided in the attempt to rationalize the role of the individual components included in the method and the effects observed on the reaction outcome. Under no circumstance should these discussions be construed as limitations of the present disclosure. In other words, the disclosure is not intended to be bound to or limited by any chemical theory, nor by any reaction mechanism suggested or discussed herein.

For the purpose of the present disclosure, reactions run at ambient temperatures are run without exercising an active control of the temperature (for example via thermostats, heating, or cooling baths).

DESCRIPTION OF EMBODIMENTS

Figure 1:
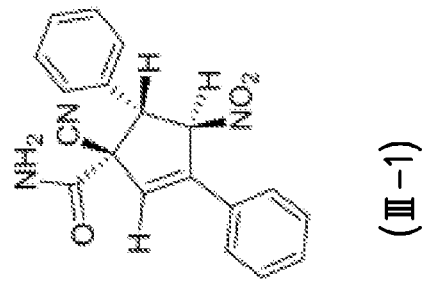
FIG. 1 shows the crystal structure of compound (III-1).
Figure 1:
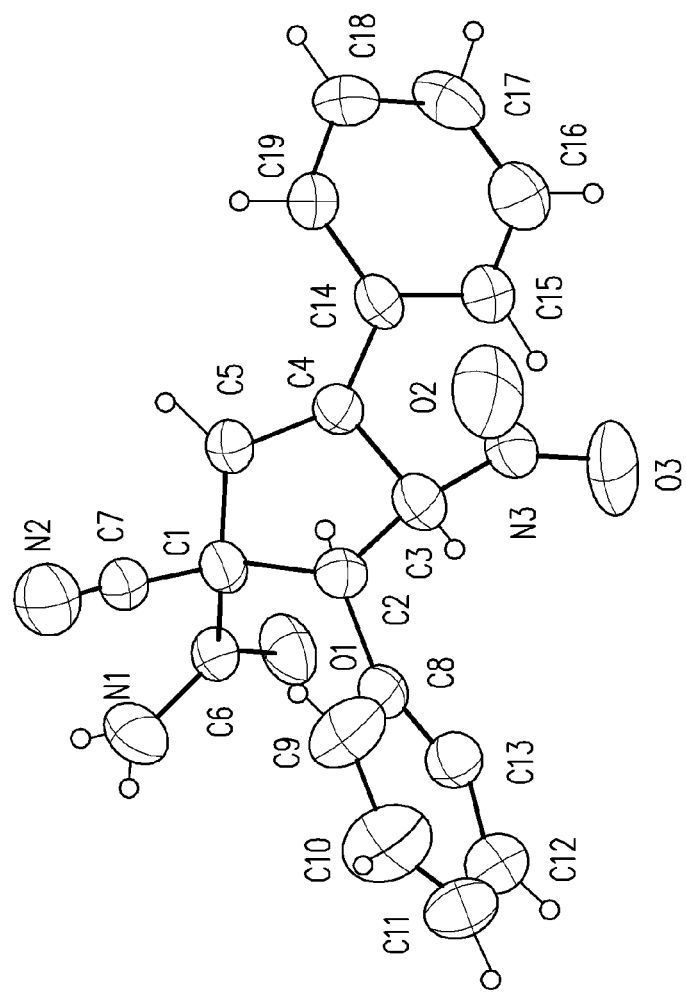

It is first noted that the term "a compound of formula (I)" is sometimes called "a compound (I)" hereafter for simplicity. The same rule applies to formulae (II) to (X) and specific examples thereof. For the sake of simplicity, unless otherwise indicated compounds of formula (III) indicates compounds having the same configuration as shown in formula (III) at the three stereogenic centers and their enantiomers. Similarly, unless otherwise indicated, compounds of formula (III-B) indicates compounds having the same configuration as shown in formula (III-B) at the three stereogenic centers and their enantiomers.

The group B in the compound of formula (I) is an unsaturated moiety, selected from substituted or unsubstituted vinylene, ethynylene, aryleneethynylene, substituted or unsubstituted arylenevinylene, and the combination thereof, such as vinylene-ethynylene (e.g. an enyne moiety), diene, triene, tetraene, polyene, diacetylene, triacetylene, arylene-vinylene, vinylene-arylene-vinylene, arylene-ethynylene, ethynylene-arylene-ethynylene, and ethylene-arylene-ethynylene. The vinylene or arylenevinylene has n substituent(s) $R^2$, wherein n is 0, 1 or 2, and when n is 2, the two $R^2$ may be the same or different, and may joint together to form a ring.

The group G in the above formulae (I)-(III) is an electron withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic and heteroaromatic groups, halogen-substituted alkyl groups, and halogen atoms.

Examples of the oxygen-containing electron-withdrawing groups include [—C(=O)$R^{10}$], wherein $R^{10}$ is selected from hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups.

Examples of the nitrogen-containing electron-withdrawing groups include cyano, nitro, and —C(=N—$R^{11}$)$R^{12}$, wherein $R^{11}$ and $R^{12}$ are the same or different in each occurrence and are independently selected from hydrogen, alkyl, aryl, and heteroaryl groups.

Examples of the sulfur-containing electron-withdrawing groups include —S(=O)$R^{13}$ and —S(=O)$_2R^{14}$. $R^{13}$ and $R^{14}$ are the same or different at each occurrence and are independently selected from hydrogen, alkyl, aryl, heteroaryl, alkoxy, aryloxy, heteroaryloxy, amino, alkylamino, dialkylamino, arylamino, diarylamino, alkylarylamino, and hydroxyl groups.

Examples of the phosphorous-containing electron-withdrawing groups include —P(=O)$R^{15}R^{16}$ and —P(=O)$_2$$R^{17}$. $R^{15}$, $R^{16}$ and $R^{17}$ are the same or different and are independently selected from hydrogen, alkyl, aryl, heteroaryl, alkoxy, aryloxy, heteroaryloxy, alkylthio, arylthio, heteroarylthio, amino, alkylamino, dialkylamino, arylamino, diarylamino, alkylarylamino, and hydroxyl groups.

Examples of the electron-withdrawing aromatic groups include aryl rings having one or more electron-withdrawing groups, and electron-withdrawing heteroaryl groups. Examples of the aryl rings having one or more electron-withdrawing groups include —$CF_3$-substituted aryl, $NO_2$-substituted aryl, carbonyl-substituted aryl, halogen-substituted aryl, and cyano-substituted aryl. Examples of the electron-withdrawing heteroaryl groups include the substituent ring derived from pyridine, pyrimidine, imidazole, purine, adenine, guanine, cytosine, uracil, thymine, and histidine.

Examples of the halogen-substituted alkyl groups include α-halo-substituted alkyl groups, α-dihalo-substituted alkyl groups, α-trihalomethyl groups, perhaloalkyl groups, and the like.

The preferred electron withdrawing group G is selected from the group consisting of $NO_2$, CN, formyl, acyl, alkylacyl, arylacyl, alkoxycarbonyl, aryloxycarbonyl, amido, carboxy, ester, amide, alkanoate, alkanoic acid, nitrile, alkanal, alkanone, sulfinyl, sulfonyl, sulfonate, alkylphosphine oxide, arylphosphine oxide, alkylphosphinate, arylphosphinate, alkylphosphonate, or arylphosphonate.

<Substituent $R^1$ and $R^2$ in Formulae (I), (III), and (IV) and $R^3$, $R^4$, and $R^5$ in Formulae (II), (III), and (IV)>

Each of $R^1$ and $R^2$ in formulae (I), (III) and (IV) is independently selected from the group consisting of hydrogen, deuterium, substituted and unsubstituted alkyl, alkenyl, alkynyl, alkenynyl, aryl, alkylaryl, arylalkyl, allyl, benzyl, cycloalkyl, cycloalkenyl, cycloalkynyl, cycloalkenynyl, alkanoyl, aryloyl, alkylsilyl, arylsilyl, alkoxysilyl, aryloxysilyl, alkoxycarbonyl, aryloxycarbonyl, heterocyclic ring, heteroaromatic ring, alkylsulfinyl, arylsulfinyl, alkylsulfonyl, arylsulfonyl, derivatives of various acid functional groups including phosphonic acid, phosphinic acid, boric acid, carboxylic acid, sulfinic acid, sulfonic acid, sulfamic acid, and amino acid, wherein the acid derivatives may include ester, amide and metal salt; aliphatic moieties having a repeating unit of $-(OCH_2CH_2)_qOCH_3$, $-(OCH_2CH(CH_3))_qOCH_3$ $-(CH_2)_qCF_3$, $-(CF_2)_qCF_3$ or $-(CH_2)_qCH_3$, wherein $q \geq 1$; and aliphatic chains having a moiety of $(OR^{18})_rOR^{19}$, wherein $R^{18}$ is a divalent $C_{1-7}$ alkylene moiety, $R^{19}$ is $C_{1-20}$ alkyl, and $1 \leq r \leq 50$. All the above mentioned substituent groups may be further substituted with allowable functional groups, such as ester, amino acid, halo, epoxy, amino, amido, acyl, organosilyl, organotin, organogermyl, nitro, alkoxy, aryloxy, alkyl, aryl, heteroaryl, alkylthio, heteroarylthio, arylthio groups, and derivatives of various acid functional groups including phosphonic acid, phosphinic acid, boric acid, carboxylic acid, sulfinic acid, sulfonic acid, sulfamic acid, and amino acid, wherein the acid derivatives may include ester, amide and metal salt.

The groups $R^1$ and $R^2$, or $R^1$ and the substituent group of G, or $R^2$ and the substituent group of G may joint together to form a substituted or unsubstituted alkylene, alkenylene, or alkynylene chain completing a heteroalicyclic or alicyclic ring system, which may include one or more heteroatoms and/or divalent moieties such as nitrogen, sulfur, sulfinyl, sulfonyl, phosphorus, selenium, tellurium, ester, carbonyl, and oxygen, wherein permissible substituents are the aforementioned functional groups.

Each $R^3$ and $R^4$ in formulae (II), (III), and (IV) is selected from the permissible groups listed above for $R^1$ and $R^2$.

Each $R^5$ in formulae (II), (III), and (IV) is selected from the permissible electron-withdrawing groups listed above for G.

Two of the groups $R^3$, $R^4$, and $R^5$ may joint together to form a substituted or unsubstituted alkylene, alkenylene, or alkynylene chain completing a heteroalicyclic or alicyclic ring system, which may include one or more heteroatoms and/or divalent moieties such as nitrogen, sulfur, sulfinyl, sulfonyl, phosphorus, selenium, tellurium, ester, carbonyl, and oxygen, wherein permissible substituents are the aforementioned functional groups.

<Substituents $R^6$, $R^7$, $R^8$ and $R^9$ in Formulae (V) and (VI)>

Each $R^6$, $R^7$, $R^8$ and $R^9$ in formulae (V) and (IV) is independently selected from the permissible groups listed above for $R^1$ and $R^2$.

Two of the groups $R^6$, $R^7$, $R^8$, and $R^9$ may joint together with each other to form a substituted or unsubstituted alkylene, alkenylene, or alkynylene chain completing a heteroalicyclic or alicyclic ring system, which may include one or more heteroatoms and/or divalent moieties such as nitrogen, sulfur, sulfinyl, sulfonyl, phosphorus, selenium, tellurium, ester, carbonyl, and oxygen, wherein permissible substituents are the aforementioned functional groups. $R^9$ is hydrogen, a substituent selected from the permissible groups listed above for $R^6$, $R^7$, and $R^8$, or an electron withdrawing group selected from the aforementioned permissible groups of G.

<Aromatic Groups for $R^1$, $R^2$, $R^3$, $R^4$, $R^5$, $R^6$, $R^7$, $R^8$ and $R^9$ in Formulae (I) to (VI)>

As described above, each of $R^1$, $R^2$, $R^3$, $R^4$, $R^5$, $R^6$, $R^7$, $R^8$, and $R^9$ in formulae (I) to (VI) can be a substituted or unsubstituted, mono- or poly-nuclear, aryl or heteroaryl. The aryl and heteroaryl preferably denote a mono-, bi- or tricyclic aromatic or heteroaromatic group with up to 25 carbon atoms that may also comprise condensed rings and is optionally substituted. Preferred aryl groups include, without limitation, benzene, biphenylene, triphenylene, naphthalene, anthracene, binaphthylene, phenanthrene, pyrene, dihydropyrene, chrysene, perylene, tetracene, pentacene, benzpyrene, fluorene, indene, indenofluorene, spirobifluorene, and the like. Preferred heteroaryl groups include, without limitation, 5-membered rings like pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings like pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, and fused systems like carbazole, indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, dithienopyridine, isobenzothiophene, dibenzothiophene, benzothiadiazothiophene, or combinations thereof. The heteroaryl groups may be substituted with allowable functional groups, such as acid, ester, amino acid, halo, epoxy, amino, silyl, nitro, alkoxy, aryloxy, arylthio, arylthio, alkyl, fluoro, fluoroalkyl, or further aryl or heteroaryl substituents.

<Base Catalyst>

Useful bases for implementing this invention include bases that have a conjugate acid with a $pK_a$ in the range from 1 to 15, more preferably in a range of 1 to 13.5. Exemplary bases includes bases containing carbonate and bicarbonate anions, nitrogen-containing bases such as 1,8-diazabicyclo[5.4.0]undec-7-ene (DBU), 1,4-diazabicyclo[2.2.2]octane (DABCO), amines, alkyl- or aryl-substituted amines, substituted and unsubstituted anilines and polyanilines, N-substituted polyanilines, N,N'-diphenyl-1,4-phenylenediimine (PDI), oligomeric anilines, phenyl-caped oligomeric anilines; N-containing heterocycles such as substituted and unsubstituted pyridines, pyrimidines, imidazoles, purines, adenines, guanines, histidines, pyrrolidine, piperidine, and morpholine; fluoride containing bases, including organic fluoride salts, such as alkylammonium fluorides, and tetraalkylammonium fluorides; inorganic fluoride salts containing cations of alkali metals, alkaline earth metals, transitional metals, or main group elements, such as sodium fluoride, potassium fluoride, caesium fluoride, calcium fluoride, magnesium fluoride, copper(II) fluoride, cuprous fluoride, silver fluoride, and ammonium fluoride; acid fluoride salts that contain bifluoride anion (e.g., $HF_2^-$) or other polymeric fluoride anions ($H_xF_{x+1}^-$, such as $H_2F_3^-$, $H_3F_4^-$, $H_4F_5^-$); and trifluoride salts ($F_3^-$). Preferred bases are the fluoride containing bases, such as organic fluoride salts, inorganic fluoride salts, acid fluoride salts. More preferred bases are organic fluoride salts such as tetraalkylammonium fluorides.

The bases described above can be used either alone or as a mixture with one or more bases. The amount of base used to implement this invention can vary widely. Amounts of bases as low as 0.01 mol % (with respect to the moles of compound of formula (II) used) are effective in promoting the reaction. Increasing the amount of base in general leads to a reduction in the reaction times, with only small effects on the yield and diastereoselectivity of the reaction. In some embodiments, the molar ratio of the base to the compound of formula (II) is in the range of 0.001 to 10, more preferably in the range of 0.001 to 0.5. Use of too strong a base might result in complex reaction mixtures and loss of diastereoselectivity.

<Solvents>

The reactive starting molecules used in the present disclosure can be either in a neat liquid form, a pure solid form, or a molten form, or as a solute form dissolving or dispersing in a given solvent medium. The resultant mixture may form a single miscible liquid phase at the first moment, or it can form initially a biphasic liquid/liquid or liquid/solid mixture that may then gradually turn into a monophasic mixture as the reaction proceeds with time.

Any solvent or solvent mixture can be used as the desirable solvent medium in implementing the present invention as long as it can help dissolve or disperse, mix or contact the reactive starting molecules and the base catalyst. Illustrative useful solvents include alcohols, linear and cyclic ethers, esters, hydrocarbons, halogen-containing hydrocarbons, substituted aromatics, ketones, amides, nitriles, carbonate esters, sulfoxides and other sulfur-containing solvents, nitroalkanes, and mixtures thereof.

Exemplary alcohols include methanol, ethanol, isopropanol, and the like. Illustrative linear and cyclic ethers include tetrahydrofuran (THF), tetrahydropyran, 2-methyltetrahydrofuran, diethyl ether, diglyme, glyme, dipropyl ether, dibutyl ether, methyl butyl ether, diphenyl ether, dioxane, diethylene glycol, ethylene glycol (EG), and the like. Illustrative aliphatic hydrocarbons include hexane, heptane, octane, nonane, decane, and the like. Exemplary halogen-containing hydrocarbons, include dichloromethane, chloroform, 1,2-dichloroethane, carbon tetrachloride, dichloroethane, dichloroethene, dibromoethane, trichloroethane, tetrachloroethane, tetrachloroethene, tribromoethane, and the like. Illustrative substituted aromatics include xylene, anisole, toluene, benzene, cumene, mesitylene, phenol, cresol, nitrobenzene, dichlorobenzene, chlorobenzene, and the like. Exemplary ketones include acetone, propanone, butanone, pentanone, hexanone, heptanone, octanone, acetophenone, and the like. Exemplary esters include ethyl acetate, methyl acetate, methyl propanoate, methyl butanoate, methyl pentanoate, and the like. Illustrative amides include N,N-dimethylformamide (DMF), N,N-dimethylacetamide, N-methylacetamide, acetamide, formamide, N-methyl-2-pyrrolidinone, 2-pyrrolidinone and the like. Exemplary nitriles include acetonitrile, propionitrile, benzonitrile, butyronitrile, and the like. Illustrative sulfoxides and other sulfur containing solvents include dimethylsulfoxide (DMSO), dimethylsulfone, and the like. Illustrative nitro substituted alkanes and aromatics include nitromethane, nitroethane, nitropropane, nitroisopropane, (nitromethyl)benzene, and the like. Exemplary carbonate esters include propylene carbonate, ethylene carbonate, butylene carbonate and the like. In general, the amount of solvent or solvent mixture employed for the reaction medium is not critical, so long as the reactive starting molecules and the base catalyst can be dissolved or dispersed, mixed or contacted with each other. Preferred solvents for the reaction are polar aprotic solvents, such as nitrile solvents, amides solvents, and sulfur containing solvents. Particularly preferred solvents are N,N-dimethylformamide and dimethylsulfoxide.

The polarity and solvation behaviour of the solvent might affect the observed diastereoselectivity of the reaction. Without being bound to or limited by any chemical theory or mechanistic proposal, it is possible that more polar solvents might better polarize the C—H bond of the activated methylene of the compound of formula (II), increasing the proton tendency to interact with the base in the initial steps of the reaction. In the case of polar protic solvents, stronger solvation interaction of the solvent with the base might interfere with the formation of compounds of formulae (VII)-(IX), leading to a lower diastereoselectivity of the reaction.

<Reaction Temperature and Reaction Time>

The useful reaction temperatures can vary widely, depending on the nature of the starting molecules and the desired product of the reaction. Since this invention provides a very effective method for making homocyclic or heterocyclic compounds, most of the reactions can undergo efficiently with high yields and stereoselectivity within a reasonable time interval (such as 1 to 5 hours) at ambient temperature, without the need of heating or cooling. So, from the economical point of view, it is most desirable to perform the reaction without exercising control of the temperature, which is the most convenient and energy saving approach. In general, a temperature for the reaction may be in the range from 0 to 45° C. Higher reaction temperatures may be used if a shorter reaction time is desirable. If compounds of formulae (IV) or (V) are desired, increasing the reaction temperature (for example in a range from 50° C. to 140° C.) might be advisable. When a compound of formula (IV) is to be formed from a compound of formula (III) generated in situ, the subsequent heating step may be applied once the formation of the compound of formula (III) is completed or is deemed satisfactory. In other words, a compound of formula (III) may be formed first without heating or cooling, and heating may be applied only when a compound of formula (IV) is to be formed. In some embodiments, compound (IV) may be obtained directly from the reaction mixture of compounds (I) and (II) by performing the reaction directly at effective elevated temperatures. In other embodiments, compound (V) may be alternatively obtained by heating compounds (VI) at the effective elevated temperatures.

The useful reaction time to implement this invention can vary widely, depending on the nature of the starting molecules and the compound being aimed for. When a compound of formula (III) is desired, a reaction time from 0.1 to 5 hours might be enough for most substrates, whilst for compounds of formula (IV), the heating step might require a time from 0.5 to 20 hours.

<Different Embodiments for the Reaction Procedure>

In some embodiments of the method to produce a homocyclic or heterocyclic compound, a compound of formula (I) is reacted with a compound of formula (II) in presence of a base.

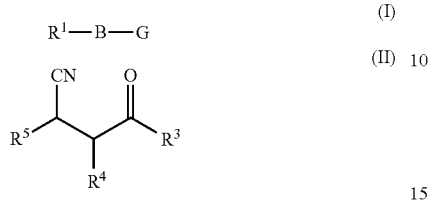

(I)
(II)

Formula (I) and (II) are as defined above. The conjugate acid of the base has a $pK_a$ in the range of 1 to 15, more preferably in a range of 1 to 13.5. In some embodiments, the base comprises a fluoride-containing base. In some embodiments, the base comprises an organic fluoride salt or an inorganic fluorides salt. In some other embodiments, the base is a tetraalkylammonium fluoride compound.

In some embodiments, the reaction is carried out in an aprotic solvent. In some other embodiments, the reaction may be carried out in a solvent having a dielectric constant of at least 6. In some embodiments, an anhydrous solvent is used to carry out the reaction.

In some embodiments, the reaction is stirred at a temperature comprised in a range from 0° C. to 45° C.

In some embodiments, a product of the reaction of a compound of formula (I) with a compound of formula (II) is a compound of formula (III).

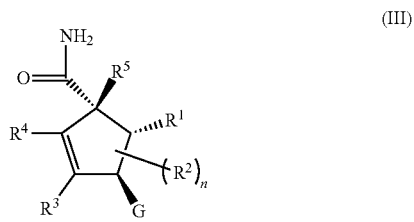

(III)

In formula (III) G, n, $R^1$, $R^2$, $R^3$, $R^4$, and $R^5$ are defined in the same manner as in formulae (I) and (II). In some embodiments, the cyclopentene compounds of formula (III) are obtained as a racemic mixture.

In some embodiments, when in the compound of formula (III) G is $NO_2$, $R^4$ is a hydrogen, and n is 0 or 1, the compound of formula (III) may be further reacted to obtain a compound of formula (IV).

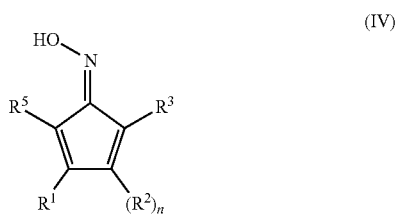

(IV)

In formula (IV), each of $R^1$, $R^2$, $R^3$, $R^5$, and n is the same as in the compound of formula (III). In some embodiments, the compound of formula (III) is purified before being reacted to form a compound of formula (IV).

In some alternative embodiments, a compound of formula (V) is formed by reacting a compound of formula (VI).

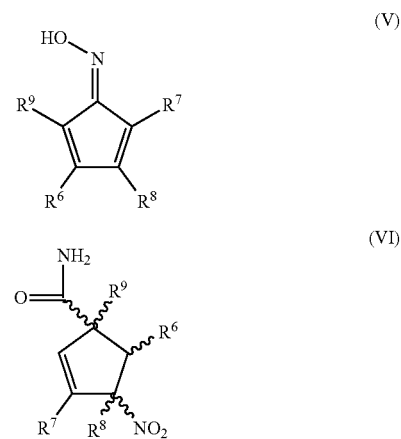

(V)
(VI)

Formula (V) and formula (VI) are as defined above. In some embodiments, the compound of formula (VI) is reacted at a temperature in a range from 50° C. to 140° C.

In some embodiments, the compound of formula (VI) is reacted in presence of a base, and a conjugated acid of the base has a $pK_a$ in a range from 1 to 15, more preferably in a range of 1 to 13.5. In some other embodiments, the base comprises a fluoride-containing ion. In some embodiments, a ratio between a number of moles of the base and a number of moles of the compound of formula (VI) is in a range from 0.001 to 10.

In some embodiments of the present disclosure, a reaction mixture comprises a compound of formula (I), a compound of formula (II) and a base.

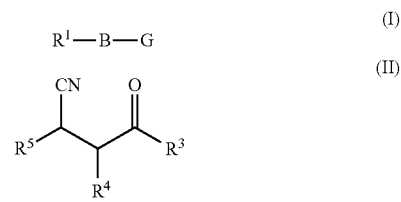

(I)
(II)

B, G, $R^1$, $R^2$, $R^3$, $R^4$, $R^5$ and n are as defined above. The conjugated acid of the base has a $pK_a$ in the range from 1 to 15, more preferably in a range of 1 to 13.5. In some embodiments, the base comprises a fluoride-containing ion. In some other embodiments, the base is an organic fluoride salt, such as a tetraalkylammonium fluoride compound.

In some embodiments, the reaction mixture comprises an aprotic solvent. In some other embodiments, the reaction mixture comprises a solvent having a dielectric constant of at least 6. In some embodiments, the reaction mixture comprises an anhydrous solvent.

In some alternative embodiments, a reaction mixture comprises a compound of formula (VI) and a base.

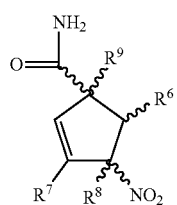

(VI)

Formula (VI) is as defined above. The conjugated acid of the base has a p$K_a$ in the range of 1 to 15, more preferably in a range of 1 to 13.5.

In some embodiments, the base comprises a fluoride-containing ion. In some embodiments, a ratio between a number of moles of the base and a number of moles of the compound of formula (VI) is in a range from 0.001 to 10, more preferably in a range of 0.001 to 0.5.

<Potential Applications>

The homocyclic or heterocyclic compounds prepared according to the present invention can be used for any purpose. For example, the compounds prepared within this invention may be used in antibacterial, pesticides, insecticides, herbicidal, or medicinal compositions. Cyclopentene derivatives accessible through the method disclosed by the present invention may show modulating activity of chemokine receptors. As such, derivatives prepared according to the present invention may be used to treat inflammatory or allergic conditions in humans or other species that would benefit from modulation of the activity of chemokine receptors. Diseases or conditions that can be treated with chemokine receptors inhibitors include anaphylactic or hypersensitization responses (e.g., allergies to drug, insect stings, or the like), inflammatory bowel diseases, autoimmune diseases (psoriasis, multiple Sclerosis, rheumatoid or psoriatic arthritis, or the like), inflammatory or allergic respiratory diseases and conditions (asthma, rhinitis, interstitials lung disease, or the like), inflammatory skin conditions (eczema, urticaria, or the like), eosinophilic conditions (eosinophilic fasciitis, myositis, pneumonia, or the like), or graft rejections.

Cyclopentadienone oximes accessible through the method disclosed by the present invention may show modulating activity for peroxisome proliferated activated receptors (PPARs). Modulators of PPARs activity may be used for treating various types of cancer and metabolic syndromes (e.g., diabetes, hyperinsulinism, arteriosclerosis obesity, hyperlipidemia, or the like).

EXAMPLES

The following examples are presented to more particularly illustrate the present invention, and should not be construed as limiting the scope and spirit of the present invention.

In the following examples, substituents are identified and referred to with the abbreviations reported in Table 1. In Table 1, * indicates a bonding site of the substituent group.

TABLE 1

Abbreviations used to indicate substituent groups

| Abbreviation | X | Y | Z | Structure |
|---|---|---|---|---|
| Ph | H | H | H | 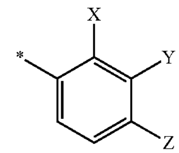 |
| oBr | Br | H | H | |
| mBr | H | Br | H | |
| mCl | H | Cl | H | |
| mNO2 | H | $NO_2$ | H | |
| mOMe | H | OMe | H | |
| pBr | H | H | Br | |
| p$CF_3$ | H | H | $CF_3$ | |
| pCl | H | H | Cl | |
| pDMA | H | H | $N(CH_3)_2$ | |
| pDPA | H | H | $N(Ph)_2$ | |
| pF | H | H | F | |
| pMe | H | H | Me | |
| p$NO_2$ | H | H | $NO_2$ | |
| pOMe | H | H | OMe | |
| BrOMe | Br | H | OMe | |
| OMe2 | OMe | H | OMe | |
| NAP | | | | 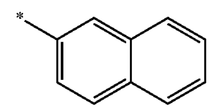 [SMILES: *c1ccc2ccccc2c1] |
| FUR | Q = O | | | 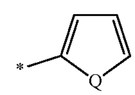 |
| PY | Q = NH | | | |
| CP | | | | 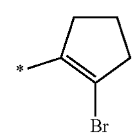 [SMILES: *C1=C(Br)CCC1] |

Tables 2 and 3 list the structures of the compounds (I-1) to (1-22) used in the following examples.

TABLE 2

Structures of compounds (I-1) to (I-18)

| Compound | $R^1$ | B | G |
|---|---|---|---|
| (I-1) | Ph | trans-HC=CH | $NO_2$ |
| (I-2) | mOMe | trans-HC=CH | $NO_2$ |
| (I-3) | pMe | trans-HC=CH | $NO_2$ |
| (I-4) | pOMe | trans-HC=CH | $NO_2$ |
| (I-5) | pDMA | trans-HC=CH | $NO_2$ |
| (I-6) | pDPA | trans-HC=CH | $NO_2$ |
| (I-7) | oBr | trans-HC=CH | $NO_2$ |
| (I-8) | mCl | trans-HC=CH | $NO_2$ |
| (I-9) | m$NO_2$ | trans-HC=CH | $NO_2$ |
| (I-10) | p$CF_3$ | trans-HC=CH | $NO_2$ |
| (I-11) | BrOMe | trans-HC=CH | $NO_2$ |
| (I-12) | $OMe_2$ | trans-HC=CH | $NO_2$ |
| (I-13) | NAP | trans-HC=CH | $NO_2$ |
| (I-14) | FUR | trans-HC=CH | $NO_2$ |
| (I-15) | PY | trans-HC=CH | $NO_2$ |
| (I-16) | CP | trans-HC=CH | $NO_2$ |
| (I-17) | pMe | trans-HC=CH | CHO |
| (I-18) | Ph | C≡C | (CO)Ph |

TABLE 3

Structures of compounds (I-19) to (I-22)

| Compound | Structure |
|---|---|
| (I-19) | NO$_2$–CH=CH–C$_6$H$_4$–CH=CH–NO$_2$ |
| (I-20) | Ph–CH=CH–CH=CH–NO$_2$ |
| (I-21) | cyclohex-2-enone |
| (I-22) | cyclohexa-2,5-diene-1,4-dione |

In Table 4 are listed the structures of the compounds (II-1) to (II-11) used in the following Examples.

TABLE 4

R$^3$, R$^4$ and R$^5$ groups in compounds (II-1) to (II-11)

| Compound | R$^3$ | R$^4$ | R$^5$ |
|---|---|---|---|
| (II-1) | Ph | H | CN |
| (II-2) | mBr | H | CN |
| (II-3) | mOMe | H | CN |
| (II-4) | pF | H | CN |
| (II-5) | pCl | H | CN |
| (II-6) | pBr | H | CN |
| (II-7) | pNO$_2$ | H | CN |
| (II-8) | pCF$_3$ | H | CN |
| (II-9) | pMe | H | CN |
| (II-10) | pOMe | H | CN |
| (II-11) | NAP | H | CN |

<General Remarks>

Unless otherwise noted, all reactions were carried out under air atmosphere. All commercial reagents were used without further purification, unless otherwise indicated. Solvents were used directly from the purchased bottles.

Compounds of formulae (I-1) to (1-22) and formulae (II-1) to (II-11) were prepared according to literature procedures (Saleh et al., *Molecules,* 2009, 14, 798; Abdelrazek et al., *J. Heterocycl. Chem.,* 2014, 51, 475; Rodriguez et al., *Tetrahedron Lett.,* 2011, 52, 2629; and references therein). The structures of the purified products were confirmed via $^1$H, $^{13}$C, DEPT, NOESY NMR, X-ray crystallography, and high-resolution mass spectrometry (HRMS).

Reported yields refer to isolated yield after purification. Diastereomeric ratios between compounds of formula (III) and compounds of formula (III-B) were determined by $^1$H NMR of the crude reaction mixture. Diastereomeric ratios between E and Z isomers for compounds of formula (IV) were determined by $^1$H NMR of the crude mixture.

All NMR spectra were recorded on a Varian 400 MHz, Bruker 400 MHz, Bruker 500 MHz, and Brucker 600 MHz spectrometers using CDCl$_3$, CD$_2$Cl$_2$ or deuterated dimethylsulfoxide (DMSO-d$_6$) as deuterated solvents. Residual peaks of the solvent were used as internal standard for calibration of $^1$H and $^{13}$C NMR spectra, whilst CFCl$_3$ (δ=0.00 ppm) was used for $^{19}$F NMR spectra as external standard.

Whenever crystal structures were deposited to the Cambridge Crystallographic Data Centre (CCDC), the CCDC reference code is reported with the crystal structure data.

<General Protocol GPI for the Reaction of Compounds of Formula (I) with Compounds of Formula (II)>

A round-bottom flask equipped with a magnetic stir bar was charged with a compound of formula (I) (0.27 mmol) and a compound of formula (II) (0.27 mmol, 1.0 equiv.) in 5 mL of solvent. In some instances, the color of the reaction mixture changed from pale yellow to pale orange upon the addition of base (0.05 equiv). The reaction mixture was stirred at ambient temperature for a time in the range from 1 to 5 h. The progress of the reaction was monitored by thin layer chromatography (TLC, SiO$_2$, eluted with ethyl acetate: hexane, 30:70, volume:volume). In some instances, as the reaction proceeded the color of the reaction mixture turned gradually from pale orange to dark brown. After complete disappearance of the starting materials, the reaction was quenched by pouring into ice cold water, resulting in formation of a precipitate. The precipitate was dissolved in ethyl acetate (15 mL) and the organic phase was washed with water (2×12 mL). The organic phase was separated and dried with anhydrous MgSO$_4$. The organic solvent was removed under reduced pressure and the obtained crude product was purified by column chromatography on silica (100-200 mesh size) using an ethyl acetate:hexane, 15:85 (volume:volume) mixture as eluent. Unless otherwise stated, a racemate of compound (III) and a racemate of the corresponding epimer (III-B) were obtained. Formation of a racemate was confirmed by single-crystal X-ray crystallography diffraction data and the inability to rotate the polarization plane of plane-polarized light.

<General Protocol GPII for the Formation of Cyclopentadienone Oximes>

A round-bottom flask equipped with a magnetic stir bar was charged with a compound of formula (III) or (VI) (0.27 mmol) in DMSO (11 mL). In some cases, the color of the reaction mixture turned from pale yellow to pale orange upon addition of 1 M TBAF in THF (0.0054 mL, 2 mol %). The reaction mixture was kept stirring at 75° C. for 6 h. The progress of the reaction was monitored by TLC (SiO$_2$, eluted with ethyl acetate:hexane, 15:85, volume:volume). In some cases, the color of the reaction mixture turned from dark brown to dark reddish over time. After disappearance of the starting material, the reaction was quenched by pouring into ice cold water, resulting in formation of a precipitate. The precipitate was dissolved in ethyl acetate (18 mL) and the organic phase was washed with water (2×12.5 mL). The organic phase was separated and dried with anhydrous MgSO$_4$. The organic solvent was removed under reduced pressure and the crude product was purified by column chromatography (SiO$_2$, 100-200 mesh, eluted with ethyl acetate:hexane, 10:90, volume:volume).

Examples 1 to 8: Solvent Screening

For Examples 1 to 8, compound (I-1) was reacted with compound (II-1) to yield compounds (III-1) and (III-B-1) according to GP1. The reactions of Examples 1 to Example 8 were performed using tetrabutylammonium fluoride (TBAF) as a base in the solvents indicated in Table 5. The reactions were stirred for 5.0 hours at ambient temperature.

TABLE 5

Results of the solvent screening

| Example | Solvent | Dielectric constant | Ratio (III-1)/(III-B-1) | Yield (III-1) (%) |
|---|---|---|---|---|
| 1 | MeOH | 33 | 50:50 | 44 |
| 2 | EtOH | 25 | 50:50 | 42 |
| 3 | 2-Propanol | 17.9 | 60:40 | 67 |
| 4 | n-Butanol | 17 | 74:26 | 60 |
| 5 | THF | 7.8 | 76:24 | 68 |
| 6 | CH$_3$CN | 38 | 79:21 | 72 |
| 7 | DMF | 37 | 91:9 | 87 |
| 8 | DMSO | 47 | 98:2 | 89 |

Racemate of 1-cyano-4-nitro-3,5-diphenylcyclopent-2-enecarboxamide (III-1)

Light brown solid, melting point: 163-165° C.;

$^1$H NMR (400 MHz, DMSO-d$_6$, δ=2.49 ppm as standard): δ 7.66 (d, J=7.4 Hz, 2H), 7.58 (s, br, 1H, NH), 7.48 (s, br, 1H, NH), 7.45-7.42 (m, 5H), 7.39-7.35 (m, 3H), 6.94 (s, 1H), 6.89 (d, J=6.0 Hz, 1H), 4.69 (d, J=6.0 Hz, 1H);

$^{13}$C NMR (100 MHz, DMSO-d$_6$, δ=39.5 ppm as standard): δ 164.6 (C), 143.7 (C), 134.0 (C), 131.4 (C), 129.7 (CH), 129.6 (CH), 128.8 (2×CH), 128.5 (3×CH), 128.4 (2×CH), 126.4 (2×CH), 118.6 (C), 93.9 (CH), 58.6 (C), 57.9 (CH);

HRMS ESI (m/z): calculated for C$_{19}$H$_{15}$N$_2$O [M−NO$_2$]$^+$ 287.1184, found 287.1181.

The crystal structure of compound (III-1) is shown in FIG. 1. In Table 6 are reported the crystal structure data with the corresponding refinement parameters.

Racemate of 1-cyano-4-nitro-3,5-diphenylcyclopent-2-enecarboxamide (III-B-1)

Light brown solid, melting point: 184-186° C.;

$^1$H NMR (400 MHz, DMSO-d$_6$, δ=2.49 ppm as standard): δ8.08 (s, br, 1H, NH), 8.02 (s, br, 1H, NH), 7.62 (d, J=8.0 Hz, 2H), 7.50-7.39 (m, 8H), 7.01 (d, J=6.2 Hz, 1H), 6.86 (s, 1H), 4.78 (d, J=6.2 Hz, 1H);

$^{13}$C NMR (100 MHz, DMSO-d$_6$, δ=39.5 ppm as standard): δ165.4 (C), 143.0 (C), 135.6 (C), 131.3 (C), 129.6 (CH), 128.9 (3×CH), 128.7 (2×CH), 128.6 (3×CH), 126.4 (2×CH), 116.8 (C), 93.8 (CH), 59.6 (C), 55.4 (CH);

HRMS ESI (m/z): calculated for C$_{19}$H$_{15}$N$_2$O [M−NO$_2$]+ 287.1184, found 287.1181.

The results in Table 5 indicate that the product (III-1) is formed in all the tested solvents, albeit with different yields and degrees of diastereoselectivity. The highest yields and ratios of compound (III-1) over (III-B-1) were obtained in Examples 5 to 8 with polar aprotic solvents. As by Example 8, DMSO yielded the highest yield and diastereoselectivity amongst the tested solvents. Amongst protic solvents, less polar solvents (n-butanol, 2-propanol) showed higher diastereoselectivity than more polar ones (MeOH, EtOH). These results indicate that in polar protic solvents, stronger solvation of the base might interfere with the interactions between the base and the reactants.

Examples 9 to 14: Use of Anhydrous Solvent

In Example 9 to Example 14, reactions between compounds of formulae (I) and (II) were run according to the general protocol GP1, in standard grade DMSO and the results were compared with the same reaction run in anhydrous DMSO. Tetrabutylammonium fluoride (TBAF) was used as a base in all cases. The reactions were stirred for 5.0 hours at ambient temperature.

TABLE 6

Crystal structure data and refinement parameters for compound (III-1)

| | | | |
|---|---|---|---|
| CCDC Code | 1585449 | Crystal size | 0.40 × 0.30 × 0.20 mm$^3$ |
| Empirical formula | C$_{19}$H$_{15}$N$_3$O$_3$ | Theta range for data collection | 4.39 to 66.41°. |
| Formula weight | 333.34 | Index ranges | −13 <= h <= 13, −8 <= k <= 8, −22 <= l <= 13 |
| Temperature | 100(2) K | Reflections collected | 10251 |
| Wavelength | 1.54178 Å | Independent reflections | 2807 [R(int) = 0.0174] |
| Crystal system | Monoclinic | Completeness to theta = 66.41° | 95.4% |
| Space group | P 1 21/n1 | Absorption correction | Semi-empirical from equivalents |
| Unit cell dimensions | a = 11.4937(2) Å<br>b = 7.5218(2) Å<br>c = 19.3250(4) Å<br>α = 90.00°<br>β = 92.4950(10)°<br>γ = 90.00° | Max. and min. transmission<br><br>Refinement method<br><br>Data/restraints/parameters | 0.9493 and 0.8718<br><br>Full-matrix least-squares on F$^2$<br>2807/0/226 |
| Volume | 1669.13(6) Å$^3$ | Goodness-of-fit on F$^2$ | 1.069 |
| Z | 4 | Final R indices [I >2 sigma(I)] | R1 = 0.0419, wR2 = 0.1078 |
| Density (calculated) | 1.327 Mg/m$^3$ | R indices (all data) | R1 = 0.0439, wR2 = 0.1095 |
| Absorption coefficient | 0.755 mm$^{-1}$ | Largest diff. peak and hole | 0.169 and −0.153 e.Å$^{-3}$ |
| F(000) | 696 | CIF-ALERTS | B |

TABLE 7

Effect of anhydrous solvents

| | | | | Standard DMSO | | Anhydrous DMSO | |
|---|---|---|---|---|---|---|---|
| Example | Compound (I) | Compound (II) | Product | Ratio (III)/(IIIB) | Yield (III) (%) | Ratio (III)/(IIIB) | Yield (III) (%) |
| 9 | (I-1) | (II-1) | (III-1) | 98:2 | 89 | >99:1 | 91 |
| 10 | (I-1) | (II-2) | (III-2) | 89:11 | 88 | 95:5 | 89 |
| 11 | (I-1) | (II-3) | (III-3) | 90:10 | 79 | 96:4 | 83 |
| 12 | (I-3) | (II-1) | (III-4) | 92:8 | 92 | 98:2 | 94 |
| 13 | (I-5) | (II-1) | (III-5) | 89:11 | 78 | 94:6 | 80 |
| 14 | (I-7) | (II-1) | (III-6) | 92:8 | 75 | 95:5 | 81 |

Example 10: Racemate of 3-(3-bromophenyl)-1-cyano-4-nitro-5-phenylcyclopent-2-enecarboxamide (III-2)

Brown solid, melting point: 192-194° C.;
$^1$H NMR (700 MHz, CDCl$_3$, δ=7.24 ppm as standard): δ 7.61 (s, 1H), 7.52 (d, J=8.05 Hz, 1H), 7.47 (d, J=7.0 Hz, 2H), 7.41-7.38 (m, 3H), 7.35 (d, J=8.05 Hz, 1H), 7.26 (t, J=8.05 Hz, 1H), 6.68 (d, J=8.7 Hz, 1H), 6.27 (s, 1H), 6.03 (s, br, 1H, NH), 5.41 (s, br, 1H, NH), 4.67 (d, J=8.7 Hz, 1H);
$^{13}$C NMR (175 MHz, CDCl$_3$, δ=77.0 ppm as standard): δ 164.8 (C), 145.6 (C), 133.1 (CH), 132.9 (C), 130.9 (C), 130.6 (CH), 129.5 (CH), 129.3 (2×CH), 129.2 (CH), 128.3 (2×CH), 127.6 (CH), 124.6 (CH), 123.2 (C), 118.2 (C), 92.4 (CH), 59.6 (CH), 57.4 (C);
HRMS ESI (m/z): calculated for C$_{19}$H$_{15}$N$_3$O$_3$Br [M+H]$^+$ 412.0297, found 412.0294.

Example 11: Racemate of 1-cyano-3-(3-methoxyphenyl)-4-nitro-5-phenylcyclopent-2-enecarboxamide (III-3)

Brown solid, melting point: 176-178° C.;
$^1$H NMR (700 MHz, CDCl$_3$, δ=7.24 ppm as standard): δ 7.48 (d, J=7.0 Hz, 2H), 7.41-7.37 (m, 3H), 7.29 (t, J=7.7 Hz, 1H), 7.03 (d, J=7.7 Hz, 1H), 6.96 (s, 1H), 6.92 (d, J=7.7 Hz, 1H), 6.72 (d, J=9.1 Hz, 1H), 6.24 (s, 1H), 6.01 (s, br, 1H, NH), 5.30 (s, br, 1H, NH), 4.68 (d, J=9.1 Hz, 1H), 3.81 (s, 3H);
$^{13}$C NMR (175 MHz, CDCl$_3$, δ=77.0 ppm as standard): δ 164.9 (C), 159.9 (C), 147.0 (C), 132.1 (C), 131.2 (C), 130.2 (CH), 129.4 (CH), 129.2 (2×CH), 128.3 (2×CH), 126.3 (CH), 118.5 (C), 118.4 (CH), 116.0 (CH), 111.4 (CH), 92.6 (CH), 59.7 (CH), 57.4 (C), 55.3 (OCH$_3$);
HRMS ESI (m/z): calculated for C$_{20}$H$_{18}$N$_3$O$_4$ [M+H]$^+$ 364.1297, found 364.1291.

Example 12: Racemate of 1-cyano-4-nitro-3-phenyl-5-(p-tolyl)cyclopent-2-enecarboxamide (III-4)

Brown solid, melting point: 189-191° C.;
$^1$H NMR (600 MHz, DMSO-d$_6$, δ=2.49 ppm as standard): δ 7.65 (d, J=7.8 Hz, 2H), 7.57 (s, br, 1H, NH), 7.45 (s, br, 1H, NH), 7.45-7.41 (m, 3H), 7.31 (d, J=7.8 Hz, 2H), 7.16 (d, J=7.8 Hz, 2H), 6.93 (s, 1H), 6.85 (d, J=6.0 Hz, 1H), 4.64 (d, J=6.0 Hz, 1H), 2.28 (s, 3H);
$^{13}$C NMR (150 MHz, DMSO-d$_6$, δ=39.5 ppm as standard): δ 164.6 (C), 143.7 (C), 137.9 (C), 131.4 (C), 130.9 (C), 129.7 (CH), 129.6 (CH), 129.1 (2×CH), 128.9 (2×CH), 128.4 (2×CH), 126.4 (2×CH), 118.7 (C), 94.1 (CH), 58.6 (C), 57.9 (CH), 20.7 (CH$_3$);

HRMS ESI (m/z): calculated for C$_{20}$H$_{17}$N$_3$O$_3$Na [M+Na]$^+$ 370.1168, found 370.1158.

Example 13: Racemate of 1-cyano-5-(4-(dimethylamino)phenyl)-4-nitro-3-phenylcyclopent-2-ene carboxamide (III-5)

Brown solid, melting point: 201-203° C.;
$^1$H NMR (500 MHz, DMSO-d$_6$, δ=2.49 ppm as standard): δ 7.64 (d, J=7.0 Hz, 2H), 7.58 (s, br, 1H, NH), 7.46-7.41 (m, 3H; s, br, 1H, NH), 7.23 (d, J=8.5 Hz, 2H), 6.91 (s, 1H), 6.78 (d, J=6.5 Hz, 1H), 6.67 (d, J=8.5 Hz, 2H), 4.52 (d, J=6.5 Hz, 1H), 2.88 (s, 6H);
$^{13}$C NMR (125 MHz, DMSO-d$_6$, δ=39.5 ppm as standard): δ 164.8 (C), 150.3 (C), 143.8 (C), 131.5 (C), 129.61 (CH), 129.56 (CH), 129.2 (2×CH), 128.9 (2×CH), 126.3 (2×CH), 120.4 (C), 118.9 (C), 111.9 (2×CH), 94.4 (CH), 58.7 (CH), 58.4 (C), 39.7 (2×CH$_3$);
HRMS-ESI (m/z): calculated for C$_{21}$H$_{21}$N$_4$O$_3$ [M+H]$^+$ 377.1614, found 377.1612.

Example 14: Racemate of 5-(2-bromophenyl)-1-cyano-4-nitro-3-phenylcyclopent-2-enecarboxamide (III-6)

Brown solid, melting point: 201-203° C.;
$^1$H NMR (600 MHz, DMSO-d$_6$, δ=2.49 ppm as standard): δ 7.71 (s, br, 1H, NH), 7.68 (dd, J=8.4, 1.2 Hz, 1H), 7.64 (dd, J=8.16, 1.8 Hz, 2H), 7.52 (dd, J=8.4, 1.2 Hz, 1H), 7.50 (s, br, 1H, NH), 7.46-7.42 (m, 3H), 7.39 (td, J=7.5, 1.2 Hz, 1H), 7.30 (td, J=7.5, 1.2 Hz, 1H), 6.95 (s, 1H), 6.81 (d, J=6.0 Hz, 1H), 5.20 (d, J=6.0 Hz, 1H);
$^{13}$C NMR (150 MHz, DMSO-d$_6$, δ=39.5 ppm as standard): δ 164.6 (C), 144.1 (C), 133.7 (C), 133.1 (CH), 131.3 (C), 130.9 (CH), 130.0 (CH), 129.8 (CH), 129.7 (CH), 129.1 (2×CH), 128.3 (CH), 126.8 (2×CH), 125.6 (C), 118.5 (C), 95.8 (CH), 58.5 (C), 56.5 (CH);
HRMS ESI (m/z): calculated for C$_{19}$H$_{15}$BrN$_3$O$_3$ [M+H]$^+$ 412.0297, found 412.0251.

The results of Table 7 indicate that the use of anhydrous solvent may further increase the observed diastereoselectivity and yield, suggesting that water (a strongly solvating protic solvent with high dielectric constant) might somewhat interfere with the reaction, probably through interaction with the base. In any case, according to the results in Table 7, standard grade solvents still perform remarkably well, and the use of anhydrous solvent is not to be construed as a required limitation of the present disclosure.

Examples 15 to 25: Base Screening

In Example 15 to Example 25, compound (I-1) was reacted with compound (II-1) to yield compounds (III-1) and (III-B-1). The reactions described in Example 9 to Example 19 were performed according to GP1 using DMSO as solvent and 100 mol % of the base indicated in Table 8. The reactions were stirred for 1.0 h at standard ambient temperature, with the exceptions of Examples 19, 20, and 25, which were stirred for 24 hours.

TABLE 8

Results of base screening

| Example | Solvent | Ratio (III-1)/(III-B-1) | Yield (III-1) (%) |
|---|---|---|---|
| 15 | TBAF | 95:5 | 85 |
| 16 | KF | 82:18 | 67 |
| 17 | CsF | 89:11 | 79 |
| 18 | $KHF_2$ | 83:17 | 62 |
| 19 | TBAC | — | Traces |
| 20 | TBAB | — | Traces |
| 21 | DBU | 58:42 | 43 |
| 22 | $Et_3N$ | 50:50 | 37 |
| 23 | $K_2CO_3$ | 51:49 | 35 |
| 24 | NaOH | —[a] | 17 |
| 25 | no base | — | not detected |

[a] The product mixture was too complicated to be correctly estimated.
TBAC = tetrabutylammonium chloride;
TBAB = tetrabutylammonium bromide;
DBU = (1,8-diazabicyclo[5.4.0]undec-7-ene).

The results in Table 8 indicate that a base is necessary for the reaction to proceed (cf. Example 25). The best results in terms of observed yield and diastereoselectivity were obtained in Examples 15 to 18, when the base contained fluoride ions or was likely to release fluoride ions in solution. The bases of Examples 16 to 18 were somewhat less soluble than TBAF in the solvent used, probably explaining the observed differences with Example 15. Examples 19 and 20, in which a tetrabutylammonium cation is used with different anions, further support this view. Using somewhat stronger bases as in Examples 21-23 still produced the compound of formula (III-1), albeit with poorer diastereoselectivity and lower yields. When using very strong bases, such as metal hydroxides in Example 24, the product mixture became increasingly complicated, and the isolated yield significantly worse.

Examples 26 to 51: Reactions of Compounds (I) with Compounds (II)

In Examples 26 to Example 51, reactions between compounds of formulae (I) and (II) were run according to the general protocol GP1, in standard grade DMSO and using tetrabutylammonium fluoride (TBAF) as a base in all cases. The reactions were stirred for 5.0 hours at ambient temperature.

TABLE 9

Results of Examples 26 to 51

| Example | Compound (I) | Compound (II) | Product | Ratio (III):(III-B) | Yield (III) (%) |
|---|---|---|---|---|---|
| 26 | (I-1) | (II-4) | (III-7) | 91:9 | 83 |
| 27 | (I-1) | (II-5) | (III-8) | 95:5 | 89 |
| 28 | (I-1) | (II-6) | (III-9) | 96:4 | 85 |
| 29 | (I-1) | (II-7) | (III-10) | 91:9 | 86 |
| 30 | (I-1) | (II-8) | (III-11) | 92:8 | 80 |
| 31 | (I-1) | (II-9) | (III-12) | 92:8 | 82 |
| 32 | (I-1) | (II-10) | (III-13) | 92:8 | 77 |
| 33 | (I-1) | (II-11) | (III-14) | 90:10 | 88 |
| 34 | (I-2) | (II-1) | (III-15) | 92:8 | 80 |
| 35 | (I-4) | (II-1) | (III-16) | 92:8 | 88 |
| 36 | (I-6) | (II-1) | (III-17) | 91:9 | 85 |
| 37 | (I-8) | (II-1) | (III-18) | 96:4 | 90 |
| 38 | (I-9) | (II-1) | (III-19) | 97:3 | 86 |
| 39 | (I-10) | (II-1) | (III-20) | 99:1 | 80 |
| 40 | (I-11) | (II-1) | (III-21) | 89:11 | 82 |
| 41 | (I-12) | (II-1) | (III-22) | 92:8 | 79 |
| 42 | (I-13) | (II-1) | (III-23) | 98:2 | 82 |
| 43 | (I-14) | (II-1) | (III-24) | 90:10 | 72 |
| 44 | (I-15) | (II-1) | (III-25) | 91:9 | 79 |
| 45 | (I-16) | (II-1) | (III-26) | 90:10 | 75 |
| 46 | (I-17) | (II-1) | (III-27) | >99:1 | 82 |
| 47 | (I-18) | (II-1) | (X-1) | — | 92 |
| 48 | (I-19) | (II-1) | (III-28) | 95:5 | 79 |
| 49 | (I-20) | (II-1) | (III-29) | 84:16 | 75 |
| 50 | (I-21) | (II-1) | (X-2) | — | 78 |
| 51 | (I-22) | (II-1) | (X-3) | — | 87 |

Example 26: Racemate of 1-cyano-3-(4-fluorophenyl)-4-nitro-5-phenylcyclopent-2-enecarboxamide (III-7)

Brown solid, melting point: 198-200° C.;
$^1$H NMR (500 MHz, $CDCl_3$, δ=7.24 ppm as standard): δ7.47 (dd, J=8.5, 2.0 Hz, 2H), 7.44 (dd, J=8.5, 5.0 Hz, 2H), 7.41-7.40 (m, 3H), 7.08 (t, J=8.7 Hz, 2H), 6.69 (d, J=8.2 Hz, 1H), 6.19 (s, 1H), 6.02 (s, br, 1H, NH), 5.33 (s, br, 1H, NH), 4.69 (d, J=8.2 Hz, 1H);
$^{13}$C NMR (125 MHz, $CDCl_3$, δ=77.0 ppm as standard): δ164.9 (C), 164.6 (d, J(C,F)=250.0 Hz, C), 146.0 (C), 131.1 (C), 129.5 (CH), 129.3 (2×CH), 128.3 (2×CH), 128.1 (d, J(C,F)=8.7 Hz, 2×CH), 127.1 (d, J(C,F)=3.7 Hz, C), 126.1 (CH), 118.4 (C), 116.4 (d, J(C,F)=21.2 Hz, 2×CH), 92.6 (CH), 60.0 (CH), 57.4 (C);
HRMS ESI (m/z): calculated for $C_{19}H_{15}N_3O_3F$ [M+H]$^+$ 352.1097, found 352.1090.

Example 27: Racemate of 3-(4-chlorophenyl)-1-cyano-4-nitro-5-phenylcyclopent-2-enecarboxamide (III-8)

Light brown solid, melting point: 203-205° C.;
$^1$H NMR (400 MHz, DMSO-$d_6$, δ=2.49 ppm as standard): δ7.46 (d, J=7.6 Hz, 2H), 7.45 (t, J=5.6 Hz, 1H), 7.40-7.37 (m, 4H), 7.39 (d, J=7.6 Hz, 2H), 6.69 (d, J=8.4 Hz, 1H), 6.23 (s, 1H), 6.05 (s, br, 1H, NH), 5.50 (s, br, 1H, NH), 4.67 (d, J=8.4 Hz, 1H);
$^{13}$C NMR (100 MHz, DMSO-$d_6$, δ=39.5 ppm as standard): δ164.9 (C), 145.8 (C), 136.2 (C), 131.0 (C), 129.5 (CH), 129.4 (2×CH), 129.3 (C), 129.2 (2×CH), 128.3 (2×CH), 127.4 (2×CH), 126.8 (CH), 118.3 (C), 92.5 (CH), 59.6 (CH), 57.4 (C);
HRMS ESI (m/z): calculated for $C_{19}H_{14}N_3O_3ClNa$ [M+Na]$^+$ 390.0621, found 390.0614.

Example 28: Racemate of 3-(4-bromophenyl)-1-cyano-4-nitro-5-phenylcyclopent-2-enecarboxamide (III-9)

Brown solid, melting point: 187-189° C.;
$^1$H NMR (500 MHz, $CDCl_3$, δ=7.24 ppm as standard): δ7.53 (d, J=8.5 Hz, 2H), 7.47 (d, J=7.0 Hz, 2H), 7.42-7.38

(m, 3H), 7.31 (d, J=8.5 Hz, 2H), 6.69 (d, J=8.75 Hz, 1H), 6.25 (s, 1H), 6.02 (s, br, 1H, NH), 5.32 (s, br, 1H, NH), 4.68 (d, J=8.75 Hz, 1H);
$^{13}$C NMR (125 MHz, CDCl$_3$, δ=77.0 ppm as standard): δ164.7 (C), 146.0 (C), 132.3 (2×CH), 130.9 (C), 129.8 (C), 129.5 (CH), 129.3 (2×CH), 128.3 (2×CH), 127.6 (2×CH), 126.8 (CH), 124.5 (C), 118.3 (C), 92.4 (CH), 59.7 (CH), 57.4 (C);
HRMS ESI (m/z): calculated for C$_{19}$H$_{14}$N$_3$O$_3$BrNa [M+Na]$^+$ 434.0116, found 434.0106.

Example 29: Racemate of 1-cyano-4-nitro-3-(4-nitrophenyl)-5-phenylcyclopent-2-enecarboxamide (III-10)

Brown solid, melting point: 173-175° C.;
$^1$H NMR (600 MHz, CDCl$_3$, δ=7.24 ppm as standard): δ8.27 (d, J=8.4 Hz, 2H), 7.63 (d, J=8.4 Hz, 2H), 7.49 (d, J=7.2 Hz, 2H), 7.44-7.41 (m, 3H), 6.75 (d, J=9.1 Hz, 1H), 6.42 (s, 1H), 6.05 (s, br, 1H, NH), 5.35 (s, br, 1H, NH), 4.70 (d, J=-9.1 Hz, 1H);
$^{13}$C NMR (150 MHz, CDCl$_3$, δ=77.0 ppm as standard): δ164.3 (C), 148.6 (C), 145.2 (C), 137.0 (C), 130.5 (C), 129.9 (CH), 129.7 (CH), 129.4 (2×CH), 128.3 (2×CH), 127.2 (2×CH), 124.2 (2×CH), 117.9 (C), 92.3 (CH), 60.4 (CH), 57.5 (C);
HRMS ESI (m/z): calculated for C$_{19}$H$_{15}$N$_4$O$_5$ [M+H]$^+$ 379.1042, found 379.1059.

Example 30: Racemate of 1-cyano-4-nitro-5-phenyl-3-(4-(trifluoromethyl)phenyl)cyclopent-2enecarboxami-de (III-11)

Brown solid, melting point: 179-181° C.;
$^1$H NMR (500 MHz, CDCl$_3$, δ=7.24 ppm as standard): δ7.66 (d, J=8.25 Hz, 2H), 7.57 (d, J=8.25 Hz, 2H), 7.49 (d, J=7.0 Hz, 2H), 7.447.40 (m, 3H), 6.74 (d, J=9.0 Hz, 1H), 6.34 (s, 1H), 6.03 (s, br, 1H, NH), 5.32 (s, br, 1H, NH), 4.70 (d, J=9.0 Hz, 1H);
$^{13}$C NMR (125 MHz, DMSO-d$_6$, δ=39.5 ppm as standard): δ164.2 (C), 142.4 (C), 135.6 (C), 133.8 (C), 132.5 (CH), 129.5 (q, J(C,F)=32.2 Hz, C), 128.6 (3×CH), 128.4 (2×CH), 128.3 (2×CH), 125.7 (2×CH), 124.0 (q, J(C,F)= 270.6 Hz, CF$_3$), 118.3 (C), 93.6 (CH), 58.5 (C), 57.9 (CH);
$^{19}$F NMR (471 MHz, DMSO-d$_6$, using CFCl$_3$ at δ=0.00 ppm as external standard) δ−61.2 (s, CF$_3$);
HRMS ESI (m/z): calculated for C$_{20}$H$_{15}$N$_3$O$_3$F$_3$[M+H]$^+$ 402.1066, found 402.1059.

Example 31: Racemate of 1-cyano-4-nitro-5-phenyl-3-(p-tolyl)cyclopent-2-enecarboxamide (III-12)

Light brown solid, melting point: 184-186° C.;
$^1$H NMR (400 MHz, DMSO-d$_6$, δ=2.49 ppm as standard): δ7.57 (s, br, 1H, NH), 7.55 (d, J=8.0 Hz, 2H), 7.46 (s, br, 1H, NH), 7.42 (d, J=8.8 Hz, 2H), 7.36-7.35 (m, 3H), 7.26 (d, J=8.0 Hz, 2H), 6.87 (s, 1H), 6.85 (d, J=5.6 Hz, 1H), 4.68 (d, J=5.6 Hz, 1H), 2.49 (s, 3H);
$^{13}$C NMR (100 MHz, DMSO-d$_6$, δ=39.5 ppm as standard): δ164.7 (C), 143.6 (C), 139.4 (C), 134.1 (C), 129.4 (2×CH), 128.7 (CH), 128.6 (C), 128.5 (3×CH), 128.4 (2×CH), 126.4 (2×CH), 118.7 (C), 94.1 (CH), 58.5 (C), 58.0 (CH), 20.8 (CH$_3$);
HRMS ESI (m/z): calculated for C$_{20}$H$_{18}$N$_3$O$_3$ [M+H]$^+$ 348.1348, found 348.1339.

Example 32: Racemate of 1-cyano-3-(4-methoxyphenyl)-4-nitro-5-phenylcyclopent-2-enecarboxamide (III-13)

Brown solid, melting point: 172-174° C.;
$^1$H NMR (700 MHz, CDCl$_3$, δ=7.24 ppm as standard): δ 7.46 (d, J=7.0 Hz, 2H), 7.38 (d, J=8.75 Hz, 2H), 7.38-7.37 (m, 3H), 6.89 (d, J=8.75 Hz, 2H), 6.68 (d, J=9.1 Hz, 1H), 6.12 (s, 1H), 6.02 (s, br, 1H, NH), 5.47 (s, br, 1H, NH), 4.67 (d, J=9.1 Hz, 1H), 3.80 (s, 3H);
$^{13}$C NMR (175 MHz, CDCl$_3$, δ=77.0 ppm as standard): δ165.4 (C), 161.0 (C), 146.3 (C), 131.5 (C), 129.3 (CH), 129.2 (2×CH), 128.3 (2×CH), 127.5 (2×CH), 124.1 (CH), 123.3 (C), 118.6 (C), 114.5 (2×CH), 92.8 (CH), 59.6 (CH), 57.4 (C), 55.4 (OCH$_3$);
HRMS ESI (m/z): calculated for C$_{20}$H$_{18}$N$_3$O$_4$ [M+H]$^+$ 364.1297, found 364.1291.

Example 33: Racemate of 1-cyano-3-(naphthalen-2-yl)-4-nitro-5-phenylcyclopent-2-enecarboxamide (III-14)

Brown solid, melting point: 198-200° C.;
$^1$H NMR (600 MHz, CDCl$_3$, δ=7.24 ppm as standard): δ 7.88 (s, 1H), 7.86 (d, J=9.0 Hz, 1H), 7.84-7.81 (m, 2H), 7.56 (dd, J=9.0, 1.8 Hz, 1H), 7.53-7.50 (m, 4H), 7.43-7.39 (m, 3H), 6.86 (d, J=9.0 Hz, 1H), 6.37 (s, 1H), 6.05 (s, br, 1H, NH), 5.36 (s, br, 1H, NH), 4.73 (d, J=9.0 Hz, 1H);
$^{13}$C NMR (150 MHz, CDCl$_3$, δ=77.0 ppm as standard): δ 165.0 (C), 146.9 (C), 133.8 (C), 133.0 (C), 131.3 (C), 129.4 (CH), 129.3 (2×CH), 129.1 (CH), 128.6 (CH), 128.4 (2×CH), 128.2 (C), 127.7 (CH), 127.3 (CH), 126.9 (CH), 126.5 (CH), 125.7 (CH), 123.3 (CH), 118.5 (C), 92.8 (CH), 59.8 (CH), 57.6 (C);
HRMS ESI (m/z): calculated for C$_{23}$H$_{18}$N$_3$O$_3$ [M+H]$^+$ 384.1348, found 384.1354.

Example 34: Racemate of 1-cyano-5-(3-methoxyphenyl)-4-nitro-3-phenylcyclopent-2-enecarboxamide (III-15)

Brown solid, melting point: 195-197° C. (79 mg, 80%);
$^1$H NMR (500 MHz, DMSO-d$_6$, δ=2.49 ppm as standard): δ 7.66 (d, J=7.0 Hz, 2H), 7.62 (s, br, 1H, NH), 7.46 (s, br, 1H, NH), 7.45-7.42 (m, 3H), 7.28 (t, J=8.0 Hz, 1H), 7.03 (s, 1H), 6.97 (d, J=8.0 Hz, 1H), 6.93 (s, 1H), 6.92 (d, J=8.0 Hz, 1H), 6.88 (d, J=6.0 Hz, 1H), 4.66 (d, J=6.0 Hz, 1H), 3.74 (s, 3H);
$^{13}$C NMR (125 MHz, DMSOd$_6$, δ=39.5 ppm as standard): δ 164.6 (C), 159.0 (C), 143.7 (C), 135.4 (C), 131.4 (C), 129.7 (CH), 129.6 (2×CH), 128.9 (2×CH), 126.5 (2×CH), 120.7 (CH), 118.7 (C), 114.6 (CH), 113.7 (CH), 94.0 (CH), 58.6 (C), 57.8 (CH), 55.0 (OCH$_3$);
HRMS ESI (m/z): calculated for C$_{20}$H$_{17}$N$_2$O$_2$ [M−NO$_2$]$^+$ 317.1290, found 317.1283.

Example 35: Racemate of 1-cyano-5-(4-methoxyphenyl)-4-nitro-3-phenylcyclopent-2-enecarboxamide (III-16)

Brown solid, melting point: 207-209° C.;
$^1$H NMR (500 MHz, DMSO-d$_6$, δ=2.49 ppm as standard): δ 7.65 (d, J=7.0 Hz, 2H), 7.59 (s, br, 1H, NH), 7.45-7.41 (m, 3H; s, br, 1H, NH), 7.36 (d, J=8.5 Hz, 2H), 6.93 (s, 1H), 6.92 (d, J=8.5 Hz, 2H), 6.83 (d, J=6.0 Hz, 1H), 4.63 (d, J=6.0 Hz, 1H), 3.74 (s, 3H);
$^{13}$C NMR (125 MHz, DMSO-d$_6$, δ=39.5 ppm as standard): δ 164.8 (C), 159.4 (C), 143.8 (C), 131.5 (C), 129.9 (2×CH), 129.7 (2×CH), 128.9 (2×CH), 126.5 (2×CH), 125.7 (C), 118.8 (C), 113.9 (2×CH), 94.3 (CH), 58.7 (C), 57.8 (CH), 55.2 (OCH$_3$);
HRMS-EI (m/z): calculated for C$_{20}$H$_{17}$N$_2$O$_2$ [M-NO$_2$]$^+$ 317.1290, found 317.1285.

Figure 2:
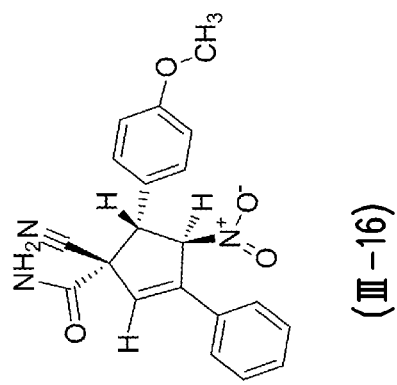
FIG. 2 shows the crystal structure of compound (III-16).
Figure 2:
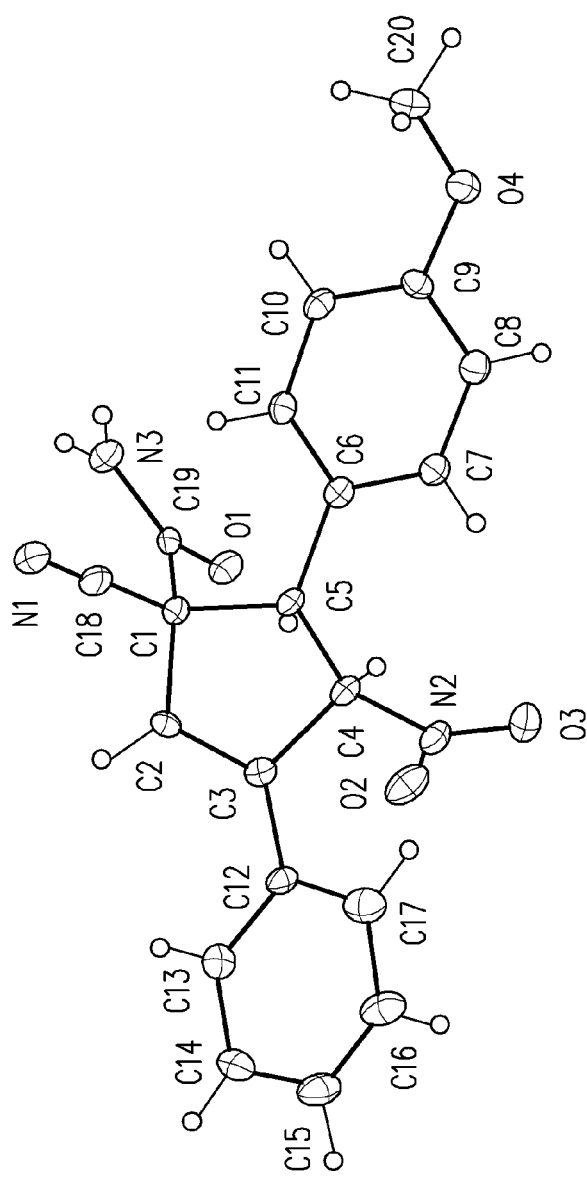

The crystal structure of compound (III-16) is shown in FIG. 2. In Table 10 are reported the crystal structure data with the corresponding refinement parameters.

TABLE 10

Crystal Structure data and refinement parameters for compound (III-16)

| | | | |
|---|---|---|---|
| CCDC Code | 1045321 | Crystal size | 0.30 × 0.28 × 0.20 mm$^3$ |
| Empirical formula | $C_{20}H_{17}N_3O_4$ | Theta range for data collection | 1.747 to 26.398°. |
| Formula weight | 363.36 | Index ranges | $-8 <= h <= 9$, $-12 <= k <= 12$, $-14 <= l <= 14$ |
| Temperature | 100(2) K | Reflections collected | 13716 |
| Wavelength | 0.71073 Å | Independent reflections | 3592 [R(int) = 0.0292] |
| Crystal system | Triclinic | Completeness to theta = 25.242° | 99.6% |
| Space group | P -1 | Absorption correction | Semi-empirical from equivalents |
| Unit cell dimensions | a = 7.7378(2) Å<br>b = 9.8726(3) Å<br>c = 11.9093(4) Å<br>α = 86.5010(15)°<br>β = 78.2460(15)°<br>γ = 81.6730(14)° | Max. and min. transmission<br><br>Refinement method<br><br>Data/restraints/parameters | 0.9485 and 0.8661<br><br>Full-matrix least-squares on F$^2$<br>3592/0/245 |
| Volume | 880.84(5) Å$^3$ | Goodness-of-fit on F$^2$ | 1.133 |
| Z | 2 | Final R indices [I >2 sigma(I)] | R1 = 0.0370, wR2 = 0.1132 |
| Density (calculated) | 1.370 Mg/m$^3$ | R indices (all data) | R1 = 0.0441, wR2 = 0.1327 |
| Absorption coefficient | 0.097 mm$^{-1}$ | Largest diff. peak and hole | 0.331 and −0.419 e.Å$^{-3}$ |
| F(000) | 380 | CIF-ALERTS | C |

Racemate of 1-cyano-5-(4-methoxyphenyl)-4-nitro-3-phenylcyclopent-2-enecarboxamide (III-B-16)

Brown solid, melting point: 212-214° C. (yield=5%);
$^1$H NMR (500 MHz, DMSO-d$_6$, δ=2.49 ppm as standard): δ 8.04 (s, br, 1H, NH), 7.99 (s, br, 1H, NH), 7.60 (d, J=7.7 Hz, 2H), 7.46-7.41 (m, 3H), 6.99-6.96 (m, 5H), 6.81 (s, 1H), 4.70 (d, J=6.5 Hz, 1H), 3.77 (s, 3H);
$^{13}$C NMR (125 MHz, DMSO-d$_6$, δ=39.5 ppm as standard): δ 165.6 (C), 159.4 (C), 143.2 (C), 131.5 (C), 130.0 (2×CH), 129.7 (CH), 129.0 (2×CH), 128.7 (CH), 127.2 (C), 126.4 (2×CH), 117.0 (C), 114.1 (2×CH), 94.1 (CH), 59.7 (C), 55.2 (CH), 55.1 (OCH$_3$);

HRMS ESI (m/z): calculated for $C_{20}H_{17}N_2O_2$ [M−NO$_2$]$^+$ 317.1290, found 317.1285.

Figure 3:
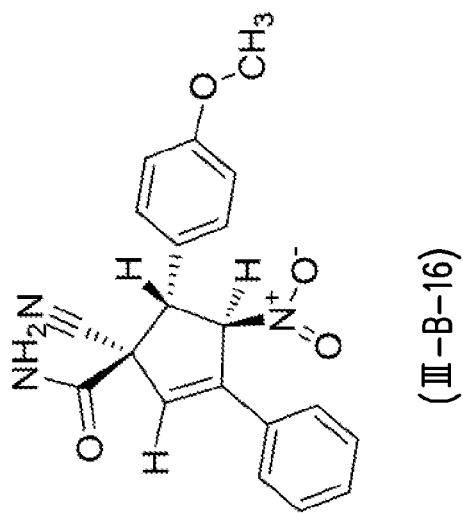
FIG. 3 shows the crystal structure of compound (III-B-16).
Figure 3:
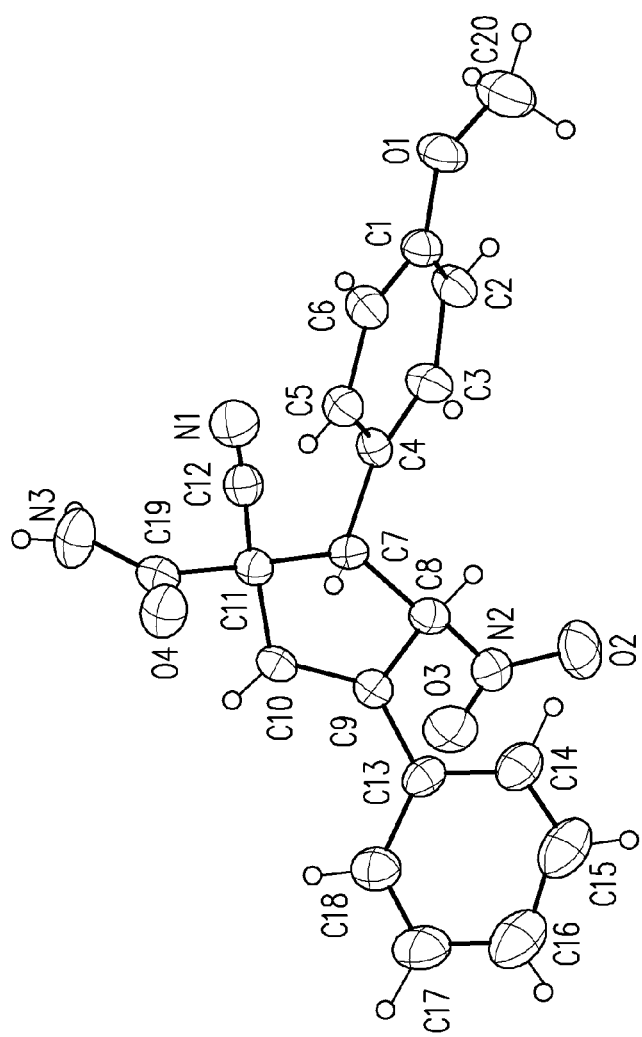

The crystal structure of compound (III-B-16) is shown in FIG. 3. In Table 11 are reported the crystal structure data with the corresponding refinement parameters.

TABLE 11

Crystal structure data and refinement parameters for compound (III-B-16)

| | | | |
|---|---|---|---|
| CCDC Code | 1045322 | Crystal size | 0.18 × 0.15 × 0.15 mm$^3$ |
| Empirical formula | $C_{20}H_{17}N_3O_4$ | Theta range for data collection | 1.72 to 26.47°. |
| Formula weight | 363.36 | Index ranges | $-7h <= 6$, $-24 <= k <= 24$, $-18 <= l <= 18$ |
| Temperature | 296(2) K | Reflections collected | 27054 |
| Wavelength | 0.71073 Å | Independent reflections | 3717 [R(int) = 0.0809] |
| Crystal system | Monoclinic | Completeness to theta = 26.47° | 98.6% |
| Space group | P 1 21/c 1 | Absorption correction | Semi-empirical from equivalents |
| Unit cell dimensions | a = 6.299(2) Å<br>b = 19.711(6) Å<br>c = 14.744(5) Å<br>α = 90.00°<br>β = 90.739(16)°<br>γ = 90.00° | Max. and min. transmission<br><br>Refinement method<br><br>Data/restraints/parameters | 0.9486 and 0.8545<br><br>Full-matrix least-squares on F$^2$<br>3717/0/246 |
| Volume | 1830.6(11) Å$^3$ | Goodness-of-fit on F$^2$ | 1.066 |
| Z | 4 | Final R indices [I >2 sigma(I)] | R1 = 0.0633, wR2 = 0.1816 |
| Density (calculated) | 1.318 Mg/m$^3$ | R indices (all data) | R1 = 0.1387, wR2 = 0.2139 |
| Absorption coefficient | 0.094 mm$^{-1}$ | Largest diff. peak and hole | 0.259 and −0.194 e.Å$^{-3}$ |
| F(000) | 760 | CIF-ALERTS | C |

Example 36: Racemate of 1-cyano-5-(4-(diphenylamino)phenyl)-4-nitro-3-phenylcyclopent-2-enecarbox amide (III-17)

Brown solid, melting point: 198-200° C.;
$^1$H NMR (500 MHz, DMSO-d$_6$, δ=2.49 ppm as standard): δ7.67 (s, br, 1H, NH), 7.64 (d, J=7.7 Hz, 2H), 7.46 (s, br, 1H, NH), 7.45-7.41 (m, 3H), 7.31 (t, J=7.5 Hz, 6H), 7.06 (t, J=7.2 Hz, 2H), 7.00 (d, J=8.5 Hz, 4H), 6.91 (s, 1H), 6.90 (d, J=7.7 Hz, 2H), 6.85 (d, J=5.7 Hz, 1H), 4.62 (d, J=5.7 Hz, 1H);
$^{13}$C NMR (125 MHz, DMSO d$_6$, δ=39.5 ppm as standard): δ164.8 (C), 147.4 (C), 146.9 (2×C), 143.7 (C), 131.4 (C), 129.7 (7×CH), 129.65 (CH), 129.62 (CH), 128.9 (2×CH), 127.4 (C), 126.5 (2×CH), 124.3 (3×CH), 123.5 (2×CH), 122.2 (2×CH), 118.7 (C), 94.1 (CH), 58.7 (CH), 57.8 (C);
HRMS ESI (m/z): calculated for C$_{31}$H$_{25}$N$_4$O$_3$ [M+H]$^+$ 501.1927, found 501.1922.

Example 37: Racemate of 5-(3-chlorophenyl)-1-cyano-4-nitro-3-phenylcyclopent-2-enecarboxamide (III-18)

Brown solid, melting point: 186-188° C.;
$^1$H NMR (600 MHz, DMSO-d$_6$, δ=2.49 ppm as standard): δ7.67 (dd, J=8.4, 1.5 Hz, 2H), 7.65 (s, br, 1H, NH), 7.54 (s, 1H), 7.52 (s, br, 1H, NH), 7.47-7.38 (m, 6H), 6.94 (s, 1H), 6.93 (d, J=5.4 Hz, 1H), 4.78 (d, J=5.4 Hz, 1H);
$^{13}$C NMR (150 MHz, DMSO-d$_6$, δ=39.5 ppm as standard): δ164.5 (C), 143.6 (C), 136.6 (C), 132.9 (C), 131.4 (C), 130.2 (CH), 129.6 (2×CH), 128.8 (2×CH), 128.5 (2×CH), 127.4 (CH), 126.5 (2×CH), 118.4 (C), 93.6 (CH), 58.5 (C), 56.8 (CH);
HRMS ESI (m/z): calculated for C$_{19}$H$_{14}$ClN$_3$O$_3$Na [M+Na]$^+$ 390.0621, found 390.0624.

Example 38: Racemate of 1-cyano-4-nitro-5-(3-nitrophenyl)-3-phenylcyclopent-2-enecarboxamide (III-19)

Brown solid, melting point: 196-198° C.;
$^1$H NMR (500 MHz, DMSO-d$_6$, δ=2.49 ppm as standard): δ 8.38 (s, 1H), 8.23 (d, J=8.0 Hz, 1H), 7.88 (d, J=7.5 Hz, 1H), 7.71-7.67 (m, 1H; s, br, 2H, NH), 7.61 (d, J=9.5 Hz, 2H), 7.48-7.42 (m, 3H), 7.02 (d, J=5.5 Hz, 1H), 6.97 (s, 1H), 5.03 (d, J=5.5 Hz, 1H);
$^{13}$C NMR (125 MHz, DMSO-d$_6$, δ=39.5 ppm as standard): δ 164.6 (C), 147.5 (C), 143.7 (C), 136.6 (C), 135.6 (CH), 131.3 (C), 129.9 (CH), 129.71 (CH), 129.69 (CH), 128.9 (2×CH), 126.6 (2×CH), 123.7 (CH), 123.5 (CH), 118.3 (C), 93.6 (CH), 58.6 (C), 56.1 (CH);
HRMS ESI (m/z): calculated for C$_{19}$H$_{14}$N$_4$O$_5$Na [M+Na]$^+$ 401.0862, found 401.0856.

Example 39: Racemate of 1-cyano-4-nitro-3-phenyl-5-(4-(trifluoromethyl)phenyl)cyclopent-2-enecarboxamide (III-20)

Brown solid, melting point: 204-206° C.;
$^1$H NMR (600 MHz, CDCl$_3$, δ=7.24 ppm as standard): δ 7.66 (d, J=8.4 Hz, 2H), 7.63 (d, J=8.4 Hz, 2H), 7.44 (dd, J=6.6, 3.0 Hz, 2H), 7.40-7.39 (m, 3H), 6.79 (d, J=8.4 Hz, 1H), 6.25 (s, 1H), 6.15 (s, br, 1H, NH), 5.52 (s, br, 1H, NH), 4.72 (d, J=8.4 Hz, 1H);
$^{13}$C NMR (150 MHz, CDCl$_3$, δ=77.0 ppm as standard): δ 164.8 (C), 146.9 (C), 135.4 (C), 131.6 (q, J(C,F)=33.0 Hz, C), 130.6 (C), 130.3 (CH), 129.1 (2×CH), 128.9 (3×CH), 126.1 (q, J(C,F)=3.7 Hz, 2×CH), 126.0 (2×CH), 125.4 (q, J(C,F)=262.0 Hz, CF$_3$), 118.2 (C), 92.4 (CH), 59.0 (CH), 57.3 (C);
HRMS-EI (m/z): calculated for C$_{20}$H$_{14}$F$_3$N$_3$O$_3$Na [M+Na]$^+$ 424.0885, found 424.0888.

Example 40: 5-(2-bromo-4-methoxyphenyl)-1-cyano-4-nitro-3-phenylcyclopent-2-enecarboxami-de (III-21)

Brown solid, melting point: 188-189° C.;
$^1$H NMR (400 MHz, DMSO-d$_6$, δ=2.49 ppm as standard): δ 7.77 (d, 2.4 Hz, 1H), 7.66 (s, br, 1H, NH), 7.65 (d, J=8.4 Hz, 2H), 7.50 (d, J=8.8 Hz, 1H), 7.47-7.41 (m, 3H), 7.26 (s, br, 1H, NH), 7.07 (d, J=7.0 Hz, 1H), 7.02 (dd, J=8.8, 2.4 Hz, 1H), 6.84 (s, 1H), 4.86 (d, J=7.0 Hz, 1H), 3.80 (s, 3H);
$^{13}$C NMR (100 MHz, DMSOd$_6$, δ=39.5 ppm as standard): δ 164.6 (C), 156.7 (C), 143.7 (C), 132.4 (CH), 131.3 (C), 131.3 (CH), 129.6 (CH), 129.3 (C), 128.8 (2×CH), 126.5 (2×CH), 124.3 (C), 118.7 (C), 113.2 (CH), 111.8 (CH), 93.4 (CH), 58.2 (C), 55.9 (CH), 51.6 (OCH$_3$);
HRMS-EI (m/z): calculated for C$_{20}$H$_{16}$BrN$_3$O$_4$Na [M+Na]$^+$ 464.0222, found 464.0201.

Example 41: Racemate of 1-cyano-5-(3,4-dimethoxyphenyl)-4-nitro-3-phenylcyclopent-2-enecarboxamide (III-22)

Brown solid, melting point: 197-199° C.;
$^1$H NMR (600 MHz, DMSO-d$_6$, δ=2.49 ppm as standard): δ 7.66 (d, J=7.2 Hz, 2H), 7.63 (s, br, 1H, NH), 7.47-7.41 (m, 5H), 7.08 (s, br, 1H, NH), 6.92 (s, 2H), 6.87 (d, J=6.0 Hz, 1H), 4.61 (d, J=6.0 Hz, 1H), 3.745 (s, 3H), 3.740 (s, 3H);
$^{13}$C NMR (150 MHz, DMSO-d$_6$, δ=39.5 ppm as standard): δ 164.8 (C), 149.0 (C), 148.3 (C), 143.8 (C), 131.5 (C), 129.6 (2×CH), 128.9 (2×CH), 126.4 (2×CH), 126.0 (C), 121.0 (CH), 118.8 (C), 112.4 (CH), 111.4 (CH), 94.5 (CH), 58.8 (C), 58.1 (CH), 55.4 (2×OCH$_3$);
HRMS-EI (m/z): calculated for C$_{21}$H$_{20}$N$_3$O$_5$ [M+H]$^+$ 394.1403, found 394.1399.

Example 42: Racemate of 1-cyano-5-(naphthalen-2-yl)-4-nitro-3-phenylcyclopent-2-enecarboxamide (III-23)

Brown solid, melting point: 207-209° C.;
$^1$H NMR (400 MHz, DMSO-d$_6$, δ=2.49 ppm as standard): δ 8.04 (s, br, 1H, NH), 7.93-7.88 (m, 3H), 7.71 (dd, J=8.2, 1.4 Hz, 2H), 7.56-7.53 (m, 4H; s, br, 1H, NH), 7.50-7.44 (m, 3H), 7.05 (d, J=5.8 Hz, 1H), 7.00 (s, 1H), 4.89 (d, J=5.8 Hz, 1H);
$^{13}$C NMR (100 MHz, DMSO-d$_6$, δ=39.5 ppm as standard): δ 164.7 (C), 143.8 (C), 132.8 (C), 132.5 (C), 131.6 (CH), 131.5 (CH), 129.8 (C), 129.7 (C), 128.9 (2×CH), 128.0 (3×CH), 127.5 (CH), 126.6 (CH), 126.5 (2×CH), 126.5 (CH), 126.1 (CH), 118.7 (C), 94.1 (CH), 58.8 (CH), 58.2 (C);
HRMS ESI (m/z): calculated for C$_{23}$H$_{18}$N$_3$O$_3$ [M+H]$^+$ 384.1348, found 384.1343.

Example 43: Racemate of 1-cyano-5-(furan-2-yl)-4-nitro-3-phenylcyclopent-2-enecarboxamide (III-24)

Brown solid, melting point: 193-195° C.;
$^1$H NMR (400 MHz, DMSO-d$_6$, δ=2.49 ppm as standard): δ 7.67 (s, br, 1H, NH), 7.65 (dd, J=1.6, 0.8 Hz, 1H), 7.61 (dd, J=8.0, 1.6 Hz, 2H), 7.48 (s, br, 1H, NH), 7.46-7.41 (m, 3H), 6.90 (s, 1H), 6.80 (d, J=6.2 Hz, 1H), 6.56 (dd, J=3.4, 0.8 Hz, 1H), 6.46 (dd, J=3.4, 1.6 Hz, 1H), 4.82 (d, J=6.2 Hz, 1H);

$^{13}$C NMR (150 MHz, CDCl$_3$, δ=77.0 ppm as standard): δ 164.8 (C), 146.6 (C), 146.1 (C), 143.7 (CH), 130.6 (C), 130.2 (CH), 129.1 (2×CH), 126.5 (CH), 126.1 (2×CH), 118.1 (C), 114.0 (CH), 109.9 (CH), 92.6 (CH), 55.8 (C), 53.2 (CH);

HRMS ESI (m/z): calculated for C$_{17}$H$_{13}$N$_2$O$_2$ [M−NO$_2$]$^+$ 277.0977, found 277.0965.

Example 44: Racemate of 1-cyano-4-nitro-3-phenyl-5-(1H-pyrrol-2-yl)cyclopent-2-ene-1-carboxamide (III-25)

Light Brown solid, melting point: 182-184° C.;

$^1$H NMR (500 MHz, CDCl$_3$, δ=7.24 ppm as standard): δ10.85 (s, br, 1H, NH), 7.64 (s, br, 1H, NH), 7.57 (d, J=7.25 Hz, 2H), 7.46-7.41 (m, 3H), 7.34 (s, br, 1H, NH), 6.87 (s, 1H), 6.72 (dd, J=3.5, 2.4 Hz, 1H), 6.70 (d, J=7.0 Hz, 1H), 6.12 (dd, J=5.6, 2.4 Hz, 1H), 5.99 (dd, J=5.6, 3.5 Hz, 1H), 4.67 (d, J=7.0 Hz, 1H);

$^{13}$C NMR (125 MHz, CDCl$_3$, δ=77.0 ppm as standard): δ164.9 (C), 143.7 (C), 131.4 (C), 129.6 (CH), 129.4 (CH), 128.8 (2×CH), 126.2 (2×CH), 123.1 (C), 118.6 (C), 118.5 (CH), 108.0 (CH), 107.8 (CH), 95.3 (CH), 58.3 (C), 52.7 (CH);

HRMS ESI (m/z): calculated for C$_{17}$H$_{14}$N$_4$O$_3$Na [M+Na]$^+$ 345.0964, found 345.09521.

Example 45: Racemate of 2'-bromo-2-cyano-5-nitro-4-phenyl-[1,1'-bi(cyclopentane)]-1',3-diene-2-carboxamide (III-26)

Brown liquid;

$^1$H NMR (600 MHz, CDCl$_3$, δ=7.24 ppm as standard): δ7.41-7.36 (m, 5H), 6.47 (s, br, 1H, NH), 6.27 (s, 1H), 6.21 (d, J=7.2 Hz, 1H), 5.96 (s, br, 1H, NH), 4.65 (d, J=7.2 Hz, 1H), 2.71-2.68 (m, 2H), 2.47-2.44 (m, 2H), 2.03-1.91 (m, 2H);

$^{13}$C NMR (150 MHz, CDCl$_3$, δ=77.0 ppm as standard): δ165.5 (C), 145.6 (C), 133.0 (C), 130.7 (C), 130.1 (CH), 129.1 (2×CH), 127.6 (CH), 127.1 (C), 126.1 (2×CH), 118.2 (C), 92.3 (CH), 55.4 (C), 54.0 (CH), 40.3 (CH$_2$), 32.0 (CH$_2$), 22.3 (CH$_2$);

HRMS ESI (m/z): calculated for C$_{18}$H$_{16}$BrN$_3$O$_3$Na [M+Na]$^+$ 424.0273, found 424.0275.

Example 46: Racemate of 1-cyano-4-formyl-3-phenyl-5-(p-tolyl)cyclopent-2-ene-1-carboxamide (III-27)

Brown solid, melting point: 187-189° C.;

$^1$H NMR (400 MHz, CDCl$_3$, δ=7.24 ppm as standard): δ9.78 (s, 1H, CHO), 7.49 (m, 5H), 7.07 (d, J=8.0 Hz, 2H), 7.03 (d, J=8.0 Hz, 2H), 5.90 (s, br, NH, 1H), 5.23 (s, br, NH, 1H), 4.92 (s, 1H), 4.20 (d, J=18.6, Hz, 1H), 3.38 (d, J=18.6 Hz, 1H), 2.28 (s, 3H, CH$_3$);

$^{13}$C NMR (100 MHz, CDCl$_3$, δ=77.0 ppm as standard): δ 188.2 (C), 165.4 (C), 158.9 (C), 138.4 (C), 137.0 (C), 132.5 (C), 132.0 (CH), 130.6 (CH), 129.4 (2×CH), 129.0 (2×CH), 128.9 (2×CH), 128.3 (2×CH), 122.0 (C), 60.4 (CH), 50.7 (C), 45.4 (CH), 21.2 (CH$_3$);

HRMS ESI (m/z): calculated for C$_{21}$H$_{18}$N$_2$O$_2$Na [M+Na]$^+$ 353.1266, found 353.1252.

Example 47: Racemate of 3-benzoyl-4-hydroxy-2,4-diphenylcyclopent-2-ene-1,1-dicarbonitrile (X-1)

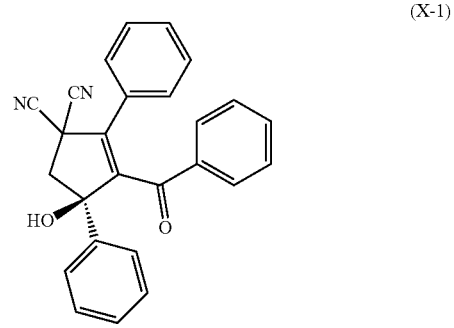 [SMILES: N#CC1(C#N)C[C@@](O)(c2ccccc2)C(C(=O)c2ccccc2)=C1c1ccccc1]

(X-1)

Brown solid, melting point: 174-176° C.;

$^1$H NMR (600 MHz, CDCl$_3$, δ=7.24 ppm as standard): δ 7.60 (dd, J=8.1, 1.09 Hz, 2H), 7.50 (dd, J=8.1, 1.09 Hz, 2H), 7.46 (dd, J=8.1, 1.5 Hz, 2H), 7.34 (t, J=7.5 Hz, 1H), 7.30 (t, J=7.8 Hz, 2H), 7.25-7.21 (m, 4H), 7.17 (t, J=8.1 Hz, 2H), 4.54 (d, 0.9 Hz, 1H, OH), 3.37 (d, J=14.4 Hz, 1H), 3.16 (dd, J=14.4, 0.9 Hz, 1H);

$^{13}$C NMR (150 MHz, CDCl$_3$, δ=77.0 ppm as standard): δ 195.1 (C), 146.5 (C), 141.9 (C), 140.9 (C), 134.6 (C), 134.2 (CH), 130.7 (CH), 130.0 (C), 129.5 (2×CH), 129.1 (2×CH), 128.9 (4×CH), 128.4 (3×CH), 124.5 (2×CH), 115.0 (C), 113.7 (C), 88.0 (C), 52.7 (CH$_2$), 42.4 (C);

HRMS ESI (m/z): calculated for C$_{26}$H$_{18}$N$_2$O$_2$Na [M+Na]$^+$ 413.1266, found 413.1274.

Figure 4:
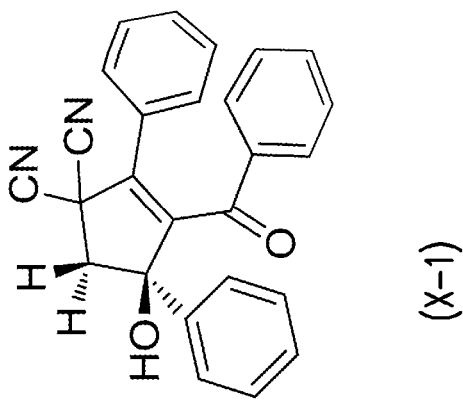
FIG. 4 shows the crystal structure of compound (X-1).
Figure 4:
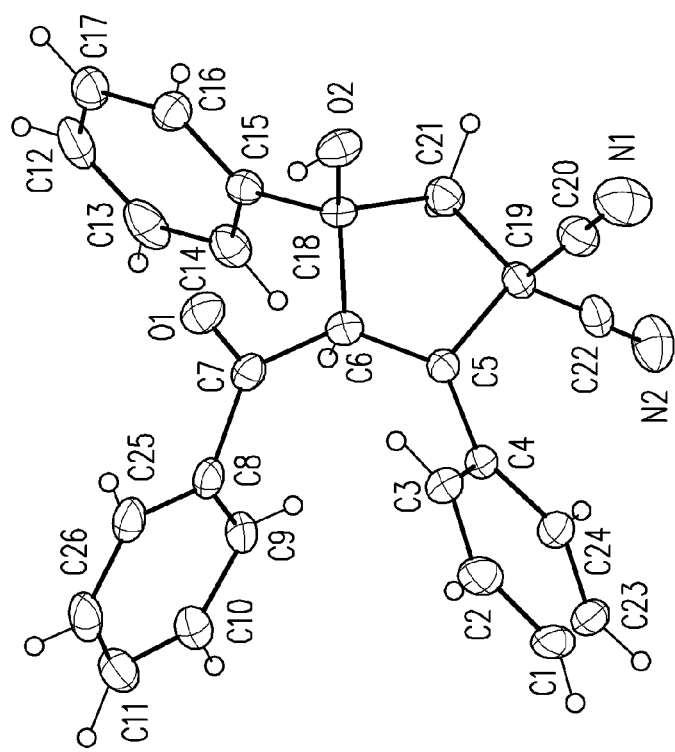

The crystal structure of compound (X-1) is shown in FIG. 4. In Table 12 are reported the crystal structure data with the corresponding refinement parameters.

TABLE 12

| Crystal structure data and refinement parameters for compound (X-1) | | | |
|---|---|---|---|
| CCDC Code | 1529387 | Crystal size | 0.30 × 0.25 × 0.15 mm$^3$ |
| Empirical formula | C$_{26}$H$_{19}$N$_2$O$_2$ | Theta range for data collection | 1.69 to 26.40°. |
| Formula weight | 391.43 | Index ranges | −10 <= h <= 10, −12 <= k <= 12, −16 <= l <= 12 |
| Temperature | 100(2) K | Reflections collected | 16096 |
| Wavelength | 0.71073 Å | Independent reflections | 4181 [R(int) =0.0278] |
| Crystal system | Triclinic | Completeness to theta = 26.40° | 99.5% |

TABLE 12-continued

Crystal structure data and refinement parameters for compound (X-1)

| | | | |
|---|---|---|---|
| CCDC Code | 1529387 | Crystal size | 0.30 × 0.25 × 0.15 mm³ |
| Space group | P -1 | Absorption correction | Semi-empirical from equivalents |
| Unit cell dimensions | a = 8.6603(3) Å<br>b = 9.9536(4) Å<br>c = 12.9050(4) Å<br>α = 108.153(2)°<br>β = 97.606(2)°<br>γ = 98.766(2)° | Max. and min. transmission<br>Refinement method<br>Data/restraints/parameters | 0.9486 and 0.8709<br><br>Full-matrix least-squares on F²<br>4181/0/272 |
| Volume | 1025.38(6) Å³ | Goodness-of-fit on F² | 1.041 |
| Z | 2 | Final R indices [I> 2sigma(I)] | R1 = 0.0418, wR2 = 0.1097 |
| Density (calculated) | 1.268 Mg/m³ | R indices (all data) | R1 = 0.0497, wR2 = 0.1154 |
| Absorption coefficient | 0.081 mm⁻¹ | Largest diff. peak and hole | 0.238 and −0.892 e.Å⁻³ |
| F(000) | 410 | CIF-ALERTS | B |

Example 48: Racemate of 5-(4-((1R,2S,5S)-2-carbamoyl-2-cyano-5-nitro-4-phenylcyclopent-3-en-1yl)phenyl)-1-cyano-4-nitro-3-phenylcyclopent-2-enecarboxamide (III-28)

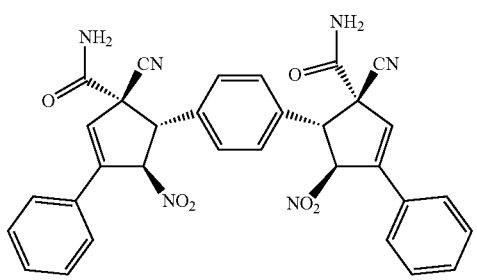

(III-28)

Brown solid, melting point: 208-210° C.;

$^1$H NMR (600 MHz, DMSO-d$_6$, δ=2.49 ppm as standard): δ7.65 (d, J=7.2 Hz, 2H), 7.64 (d, J=7.2 Hz, 2H), 7.56 (s, br, 2H, NH), 7.51-7.50 (m, 4H; 2H, NH), 7.47-7.41 (m, 6H), 6.97 (d, J=6.6 Hz, 1H), 6.95 (d, J=6.6 Hz, 1H), 6.89 (s, 2H), 4.74 (d, J=6.6 Hz, 1H), 4.73 (d, J=6.6 Hz, 1H);

$^{13}$C NMR (150 MHz, DMSO-d$_6$, δ=39.5 ppm as standard): δ164.6 (2×C), 143.9 (2×C), 133.9 (2×C), 131.5 (2×C), 129.6 (2×CH), 129.30 (2×CH), 129.25 (2×CH), 128.9 (4×CH), 128.7 (2×CH), 126.3 (2×CH), 126.3 (2×CH), 118.7 (C), 118.6 (C), 93.4 (CH), 93.3 (CH), 58.4 (C), 58.3 (C), 57.84 (CH), 57.79 (CH);

HRMS ESI (m/z): calculated for C$_{32}$H$_{25}$N$_6$O$_6$ [M+H]$^+$ 589.1836, found 589.1847.

Example 49: Racemate of 1-cyano-4-nitro-3-phenyl-5-((E)-styryl)cyclopent-2-enecarboxamide (III-29)

Light brown solid, melting point: 192-193° C.;

$^1$H NMR (700 MHz, DMSO-d$_6$, δ=2.49 ppm as standard): δ7.88 (s, br, 1H, NH), 7.70 (s, br, 1H, NH), 7.58 (dd, J=9.8, 1.4 Hz, 2H), 7.45-7.41 (m, 5H), 7.36 (t, J=8.4 Hz, 2H), 7.30 (t, J=8.4 Hz, 1H), 6.89 (s, 1H), 6.86 (d, J=18.9 Hz, 1H), 6.50 (d, J=6.3 Hz, 1H), 6.28 (dd, J=18.9 and 11.2 Hz, 1H), 4.15 (dd, J=11.2, 6.3 Hz, 1H);

$^{13}$C NMR (150 MHz, DMSO-d$_6$, δ=39.5 ppm as standard): δ165.1 (C), 143.3 (C), 135.8 (CH), 135.7 (C), 131.4 (C), 129.5 (2×CH), 128.8 (2×CH), 128.7 (2×CH), 128.4 (CH), 126.6 (2×CH), 126.3 (2×CH), 122.5 (CH), 118.4 (C), 94.5 (CH), 57.6 (C), 56.7 (CH);

HRMS ESI (m/z): calculated for C$_{21}$H$_{17}$N$_2$O [M−NO$_2$]$^+$ 313.1341, found 313.1336.

Example 50: Racemate of 1-cyano-4-oxo-3-phenyl-2,4,5,6,7,7a-hexahydro-1H-indene-1-carboxamide (X-2)

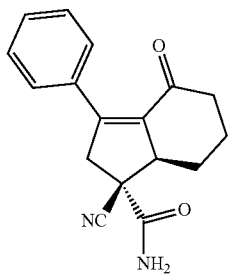

(X-2)

Brown solid, melting point: 182-184° C.;

$^1$H NMR (600 MHz, DMSO-d$_6$, δ=2.49 ppm as standard): δ 7.77 (s, br, NH, 1H), 7.73 (s, br, NH, 1H), 7.45 (dd, J=6.3, 3.3 Hz, 2H), 7.34-7.32 (m, 3H), 3.73-3.71 (m, 1H), 3.58 (dd, J=17.4, 2.4 Hz, 1H), 3.33 (dd, J=17.4, 1.2 Hz, 1H), 2.33-2.29 (m, 2H), 2.11-2.08 (m, 1H), 2.00-1.98 (m, 1H), 1.82-1.74 (m, 1H) 1.51 (qd, J=12.6, 3.6 Hz, 1H);

$^{13}$C NMR (150 MHz, DMSO-d$_6$, δ=39.5 ppm as standard): δ 199.0 (C), 166.5 (C), 143.5 (C), 134.2 (C), 133.6 (C), 128.9 (CH), 128.2 (2×CH), 127.9 (2×CH), 122.3 (C), 57.2 (CH), 47.8 (C), 45.4 (CH$_2$), 41.6 (CH$_2$), 27.2 (CH$_2$), 23.0 (CH$_2$);

HRMS ESI (m/z): calculated for C$_{17}$H$_{17}$N$_2$O$_2$ [M+H]$^+$ 281.1290, found 281.1286.

Figure 5:
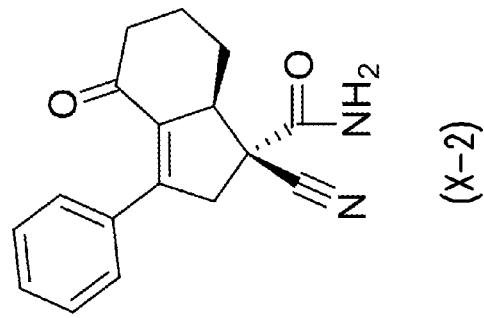
FIG. 5 shows the crystal structure of compound (X-2).
Figure 5:
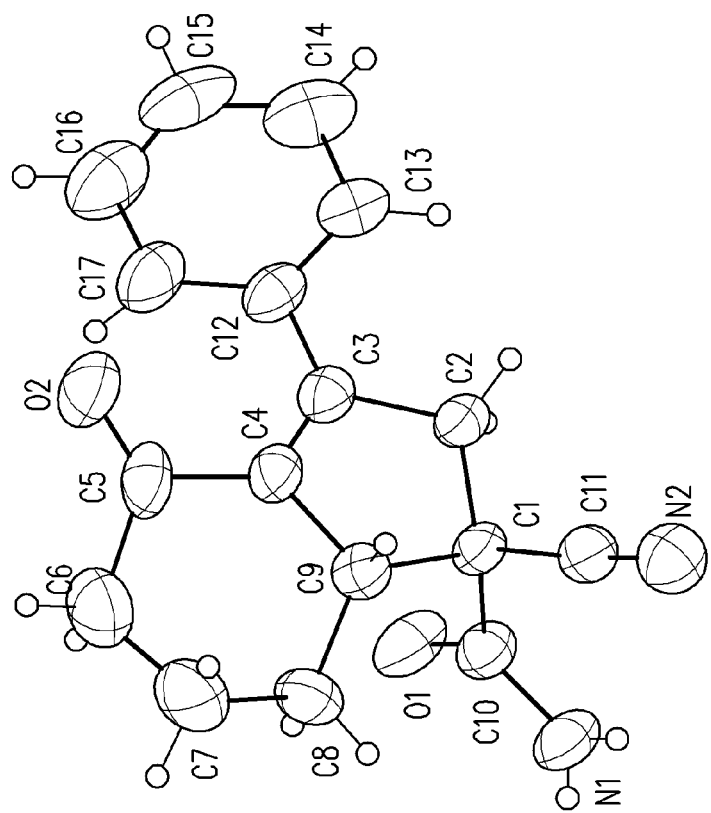

The crystal structure of compound (X-2) is shown in FIG. 5. In Table 13 are reported the crystal structure data with the corresponding refinement parameters.

TABLE 13

Crystal structure data and refinement parameters for compound (X-2)

| | | | |
|---|---|---|---|
| CCDC Code | 1529389 | Crystal size | 0.25 × 0.20 × 0.20 mm$^3$ |
| Empirical formula | $C_{17}H_{16}N_2O_2$ | Theta range for data collection | 2.50 to 26.42°. |
| Formula weight | 280.32 | Index ranges | −11 <= h <= 11, −11 <= k <= 11, 0 <= l <= 19 |
| Temperature | 296(2) K | Reflections collected | 5520 |
| Wavelength | 0.71073 Å | Independent reflections | 5531 [R(int) = 0.0000] |
| Crystal system | Monoclinic | Completeness to theta = 26.42° | 99.9% |
| Space group | P 1 21/n 1 | Absorption correction | Semi-empirical from equivalents |
| Unit cell dimensions | a = 9.3694(7) Å b = 9.4899(7) Å c = 15.8353(12) Å α = 90.00° β = 91.3220(10)° γ = 90.00° | Max. and min. transmission Refinement method Data/restraints/ parameters | 0.7454 and 0.6515 Full-matrix least-squares on F$^2$ 5531/0/191 |
| Volume | 1407.62(18) Å$^3$ | Goodness-of-fit on F$^2$ | 0.982 |
| Z | 4 | Final R indices [I >2 sigma(I)] | R1 = 0.0529, wR2 = 0.1428 |
| Density (calculated) | 1.323 Mg/m$^3$ | R indices (all data) | R1 = 0.0782, wR2 = 0.1611 |
| Absorption coefficient | 0.088 mm$^{-1}$ | Largest diff. peak and hole | 0.403 and −0.372 e.Å$^{-3}$ |
| F(000) | 592 | CIF-ALERTS | B |

Example 51: Racemate of (R)-4-cyano-6-hydroxy-2-phenyl-4H-chromene-4-carboxamide (X-3)

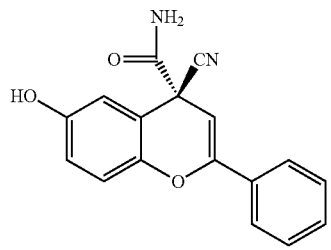

(X-3)

Brown solid, melting point: 191-193° C.;

$^1$H NMR (600 MHz, DMSO-d$_6$, δ=2.49 ppm as standard): δ 9.68 (s, 1H, OH), 7.83 (dd, J=7.8, 1.8 Hz, 2H), 7.81 (s, br, NH, 1H), 7.57 (s, br, NH, 1H), 7.49-7.45 (m, 3H), 7.16 (d, J=7.5 Hz, 1H), 6.87 (s, 1H), 6.86 (d, J=7.5 Hz, 1H), 5.97 (s, 1H);

$^{13}$C NMR (150 MHz, DMSO-d$_6$, δ=39.5 ppm as standard): δ 168.6 (C), 154.1 (C), 149.7 (C), 141.7 (C), 132.4 (C), 129.7 (CH), 128.5 (2×CH), 125.1 (2×CH), 119.5 (C), 118.7 (CH), 118.2 (CH), 115.7 (C), 112.5 (CH), 91.6 (CH), 46.3 (C);

HRMS ESI (m/z): calculated for $C_{17}H_{13}N_2O_3$ [M+H]$^+$ 293.0926, found 293.0932.

Figure 6:
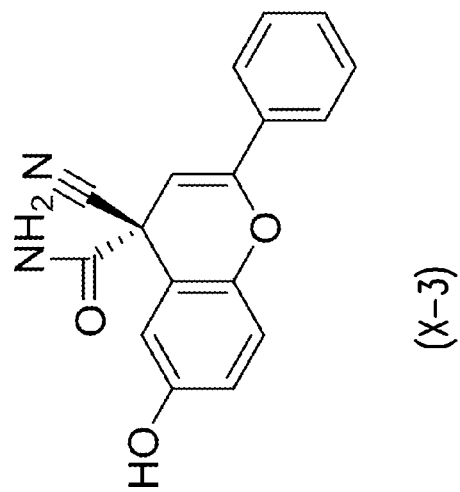
FIG. 6 shows the crystal structure of compound (X-3).
Figure 6:
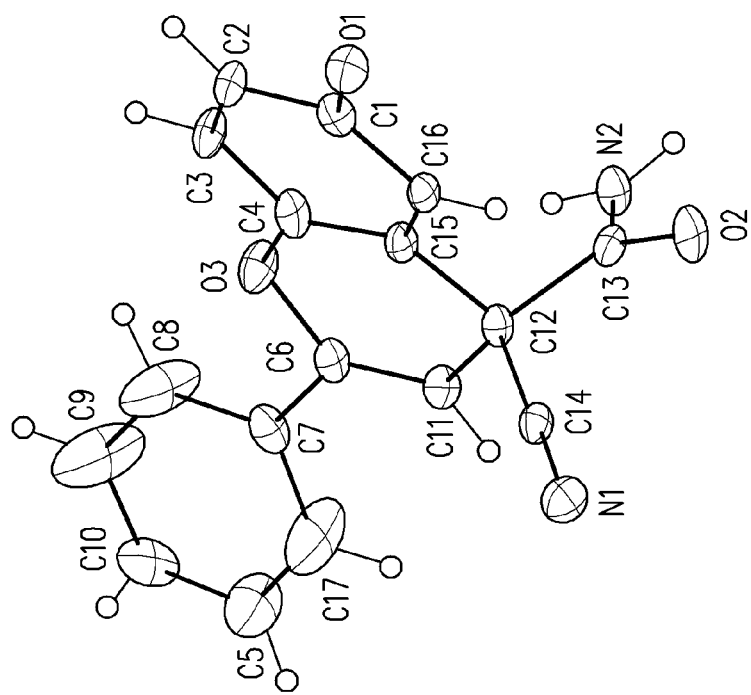

The crystal structure of compound (X-3) is shown in FIG. 6. In Table 14 are reported the crystal structure data with the corresponding refinement parameters.

TABLE 14

Crystal structure data and refinement parameters for compound (X-3)

| | | | |
|---|---|---|---|
| CCDC Code | 1529388 | Crystal size | 0.25 × 0.20 × 0.12 mm$^3$ |
| Empirical formula | $C_{17}H_{11}N_2O_3$ | Theta range for data collection | 1.44 to 26.79°. |
| Formula weight | 291.28 | Index ranges | −17 <= h <= 17, −9 <= k <= 8, −8 <= l <= 15 |
| Temperature | 100(2) K | Reflections collected | 9935 |
| Wavelength | 0.71073 Å | Independent reflections | 2801 [R(int) = 0.0236] |
| Crystal system | Monoclinic | Completeness to theta = 26.79° | 96.7% |
| Space group | P 1 21/n 1 | Absorption correction | Semi-empirical from equivalents |
| Unit cell dimensions | a = 14.165(15) Å b = 7.924(9) Å c = 12.147(12) Å α = 90.00° β = 94.54(2)° γ = 90.00° | Max. and min. transmission Refinement method Data/restraints/ parameters | 0.9486 and 0.8366 Full-matrix least-squares on F$^2$ 2801/0/199 |

TABLE 14-continued

Crystal structure data and refinement parameters for compound (X-3)

| CCDC Code | 1529388 | Crystal size | $0.25 \times 0.20 \times 0.12$ mm$^3$ |
|---|---|---|---|
| Volume | 1359(3) Å$^3$ | Goodness-of-fit on F$^2$ | 1.045 |
| Z | 4 | Final R indices [I >2 sigma(I)] | R1 = 0.0595, wR2 = 0.1472 |
| Density (calculated) | 1.423 Mg/m$^3$ | R indices (all data) | R1 = 0.0721, wR2 = 0.1573 |
| Absorption coefficient | 0.100 mm$^{-1}$ | Largest diff. peak and hole | 0.696 and −0.676 e.Å$^{-3}$ |
| F(000) | 604 | CIF-ALERTS | B |

The results in Table 9 indicate that the reaction between a compound of formula (I) and a compound of formula (II) tends to proceed with high yields and high diastereoselectivity for a broad range of substituents on each starting monomer. The reaction proceeds satisfactorily also when the compound of formula (I) is a multifunctional nitrostyrene (compound 1-19), a conjugation extended nitrostyrene (1-20), or an α,β-unsaturated carbonyl compounds (cf. the cinnamaldehyde (1-17), the ynone (1-18), cyclohexenone (1-21), or 1,4-benzoquinone (1-22)). The fact that in the case of Example 47 the observed product is a cyclopentanol preserving both cyano groups suggests that the loss of the carbonyl oxygen and the formation of the carboxamide group might be tightly linked events. Formation of compound (X-2) in Example 50 indicates that different protons than the ones adjacent to the activated methylene compound might be lost during the elimination of the hydroxyl group formed by the carbonyl of compound (II).

Examples 52 to 58: Preparation of Cyclopentadienone Oximes

Compounds (IV-1) to (VI-7) were prepared from the starting materials indicated in Table 15 following the procedure outlined in GPII.

TABLE 15

Preparation of cyclopentadienone oximes

| Example | Starting material | Product | Ratio Z:E | Yield (IV) (%) |
|---|---|---|---|---|
| 52 | (III-1) | (IV-1) | 95:5 | 82 |
| 53 | (III-2) | (IV-2) | 95:5 | 80 |
| 54 | (III-6) | (IV-3) | 99:1 | 78 |
| 55 | (III-8) | (IV-4) | 92:8 | 72 |
| 56 | (III-11) | (IV-5) | 96:4 | 80 |
| 57 | (III-15) | (IV-6) | 95:5 | 78 |
| 58 | (III-20) | (IV-7) | 92:8 | 76 |

Example 52: Preparation of (Z)-5-(hydroxyimino)-2,4-diphenylcyclopenta-1,3-diene-1-carbonitrile (IV-1)

The reaction was performed on a 1.5 mmol scale. The product was isolated as a brick red solid.

$^1$H NMR (400 MHz, CDCl$_3$, δ=7.24 ppm as standard): δ9.48 (s, OH), 7.97 (dd, J=6.0, 3.0 Hz, 2H), 7.66 (dd, J=8.0, 2.0 Hz, 2H), 7.22-7.51 (m, 3H), 7.41-7.36 (m, 3H), 7.08 (s, 1H), n-Hexane grease (1.28, 0.82);

$^{13}$C NMR (150 MHz, DMSO-d$_6$, δ=39.5 ppm as standard): δ159.4 (C), 155.8 (C), 140.5 (C), 132.2 (C), 131.7 (CH), 131.6 (C), 129.9 (CH), 129.2 (2×CH), 129.0 (2×CH), 128.8 (CH), 128.5 (2×CH), 128.1 (2×CH), 117.6 (C), 85.9 (C);

HRMS ESI (m/z): calculated for C$_{18}$H$_{12}$N$_2$ONa [M+Na]$^+$ 295.0847, found 295.0844.

Figure 7:
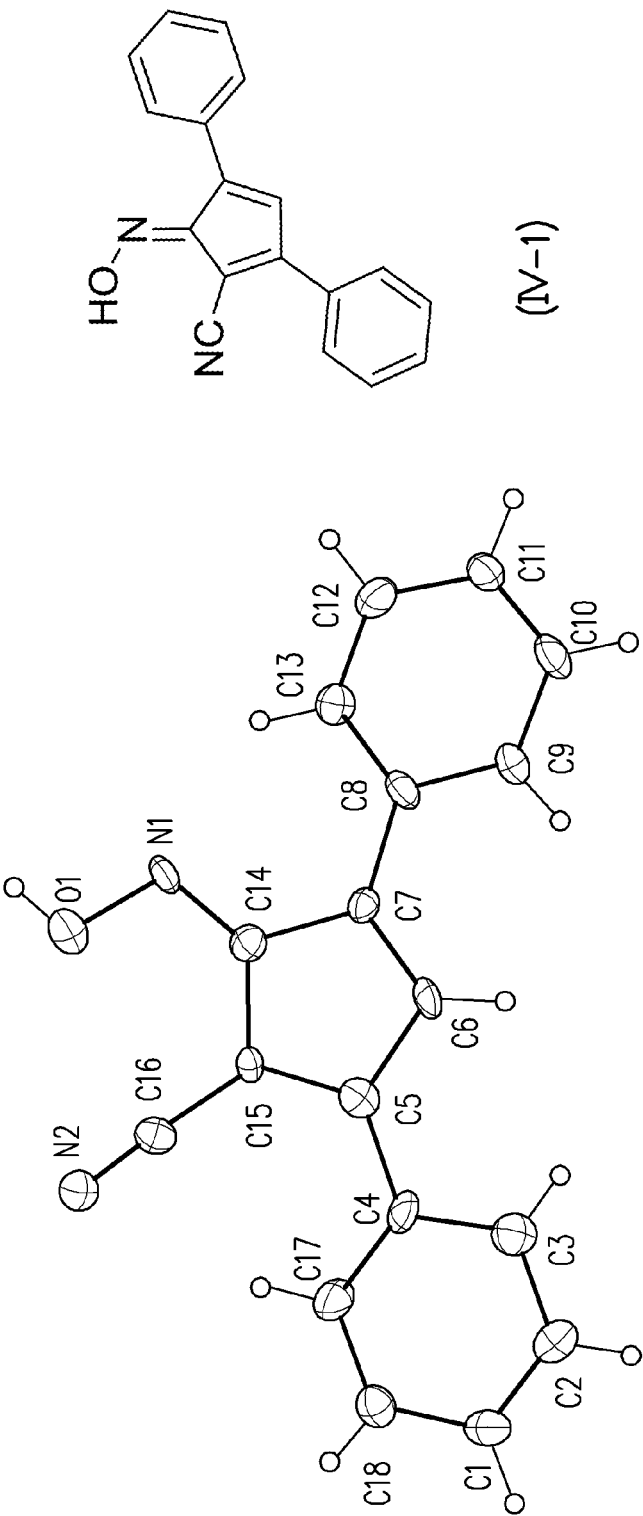
FIG. 7 shows the crystal structure of compound. (IV-1)

The crystal structure of compound (IV-1) is shown in FIG. 7. In Table 16 are reported the crystal structure data with the corresponding refinement parameters.

TABLE 16

Crystal structure data and refinement parameters for compound (IV-1)

| CCDC Code | 1816533 | Crystal size | $0.08 \times 0.02 \times 0.02$ mm$^3$ |
|---|---|---|---|
| Empirical formula | C$_{36}$H$_{24}$N$_4$O$_2$ | Theta range for data collection | 1.604 to 26.438°. |
| Formula weight | 544.59 | Index ranges | −10 <= h <=11, −14 <= k <= 14, −15 <= l <= 16 |
| Temperature | 100(2) K | Reflections collected | 18753 |
| Wavelength | 0.71073 Å | Independent reflections | 5829 [R(int) = 0.2110] |
| Crystal system | Triclinic | Completeness to theta = 25.242° | 98.6% |
| Space group | P -1 | Absorption correction | Semi-empirical from equivalents |

TABLE 16-continued

| Crystal structure data and refinement parameters for compound (IV-1) | | | |
|---|---|---|---|
| CCDC Code | 1816533 | Crystal size | 0.08 × 0.02 × 0.02 mm$^3$ |
| Unit cell dimensions | a = 9.390(3) Å<br>b = 11.561(4) Å<br>c = 12.824(4) Å<br>α = 82.956(6)°<br>β = 84.392(6)°<br>γ = 74.505(6)° | Max. and min. transmission<br><br>Refinement method<br><br>Data/restraints/<br>parameters | 0.9485 and 0.7842<br><br>Full-matrix<br>least-squares on F$^2$<br>5329/0/381 |
| Volume<br>Z | 1328.3(8) Å$^3$<br>2 | Goodness-of-fit on F$^2$<br>Final R indices<br>[I >2 sigma(I)] | 0.984<br>R1 = 0.1028,<br>wR2 = 0.2404 |
| Density (calculated) | 1.362 Mg/m$^3$ | R indices (all data) | R1 = 0.2526,<br>wR2 = 0.3188 |
| Absorption coefficient | 0.086 mm$^{-1}$ | Largest diff. peak and hole | 0.580 and −0.317 e.Å$^{-3}$ |
| F(000) | 568 | CIF-ALERTS | B |

Example 53: preparation of (Z)-4-(3-bromophenyl)-5-(hydroxyimino)-2-phenyl-cyclopenta-1,3-diene-1-carboni-trile (IV-2)

Brick red solid;
$^1$H NMR (400 MHz, CDCl$_3$, δ=7.24 ppm as standard): δ 9.28 (s, OH), 7.98 (dd, J=6.2, 2.2 Hz, 2H), 7.84 (s, 1H), 7.61 (d, J=7.6 Hz, 1H), 7.53-7.48 (m, 4H), 7.27 (d, J=7.6 Hz, 1H), 7.13 (s, 1H), n-Hexane grease (1.23, 0.86);
$^{13}$C NMR (125 MHz, DMSO-d$_6$, δ=39.5 ppm as standard): δ 159.1 (C), 155.4 (C), 138.2 (C), 134.3 (C), 131.7 (CH), 131.40 (C), 131.31 (CH), 131.27 (CH), 131.25 (CH), 130.5 (CH), 129.1 (2×CH), 128.1 (2×CH), 127.8 (CH), 121.8 (C), 117.4 (C), 86.5 (C);
HRMS ESI (m/z): calculated for C$_{18}$H$_{12}$BrN$_2$O [M+H]$^+$ 351.0133, found 351.0128.

Example 54: preparation of (Z)-2-(2-bromophenyl)-5-(hydroxyimino)-4-phenylcyclopenta-1,3-diene-1-carbonitrile (IV-3)

Figure 8:
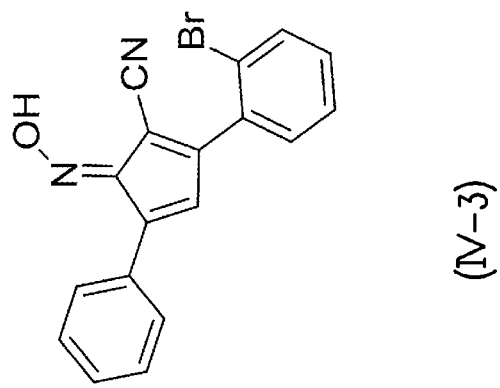
FIG. 8 shows the crystal structure of compound (IV-3)
Figure 8:
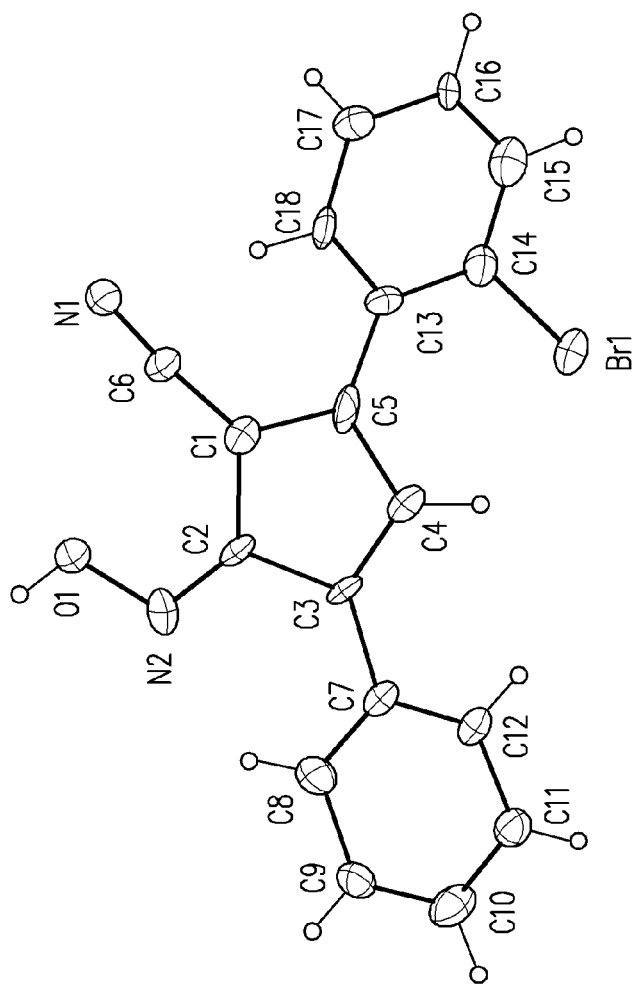

Brick red solid;
$^1$H NMR (400 MHz, CDCl$_3$, δ=7.24 ppm as standard): δ 9.45 (s, OH), 7.70 (d, J=8.0 Hz, 1H), 7.66 (dd, J=7.4, 1.2 Hz, 2H), 7.60 (d, J=7.6 Hz, 1H), 7.45 (t, J=7.6 Hz, 1H), 7.41-7.32 (m, 4H), 7.02 (s, 1H), n-Hexane grease (1.24, 0.86);
$^{13}$C NMR (100 MHz, CDCl$_3$, δ=77.0 ppm as standard): δ 162.9 (C), 156.1 (C), 139.7 (C), 133.7 (CH), 133.5 (C), 132.0 (C), 131.8 (CH), 131.7 (C), 130.6 (CH), 129.0 (2×CH), 128.9 (CH), 128.5 (2×CH), 127.8 (CH), 121.8 (C), 116.2 (C), 92.0 (C), n-Hexane grease (31.9, 29.7, 22.7, 14.1);
HRMS ESI (m/z): calculated for C$_{18}$H$_{12}$BrN$_2$O [M+H]$^+$ 351.0133, found 351.0133.
The crystal structure of compound (IV-3) is shown in FIG. 8. In Table 17 are reported the crystal structure data with the corresponding refinement parameters.

TABLE 17

| Crystal structure data and refinement parameters for compound (IV-3) | | | |
|---|---|---|---|
| CCDC Code | 1817817 | Crystal size | 0.1 × 0.01 × 0.01 mm$^3$ |
| Empirical formula | C$_{18}$H$_{11}$BrN$_2$O | Theta range for data collection | 1.826 to 26.454°. |
| Formula weight | 351.20 | Index ranges | −4 <= h <= 4,<br>−404 <= k <= 40,<br>−13 <= l <= 13 |
| Temperature | 100(2) K | Reflections collected | 4971 |
| Wavelength | 0.71073 Å | Independent reflections | 2522<br>[R(int) = 0.1070] |
| Crystal system | Monoclinic | Completeness to theta = 25.242° | 91.9% |
| Space group | P 21/c | Absorption correction | Semi-empirical from equivalents |
| Unit cell dimensions | a = 3.8844(14) Å<br>b = 32.965(10) Å<br>c = 11.151(4) Å<br>α = 90°<br>β = 90°<br>γ = 90° | Max. and min. transmission<br><br>Refinement method<br><br>Data/restraints/<br>parameters | 0.9485 and 0.5512<br><br>Full-matrix<br>least-squares on F$^2$<br>2522/0/202 |
| Volume<br>Z | 1427.8(8) Å$^3$<br>4 | Goodness-of-fit on F$^2$<br>Final R indices<br>[I >2 sigma(I)] | 1.011<br>R1 = 0.0865,<br>wR2 = 0.1733 |
| Density (calculated) | 1.634 Mg/m$^3$ | R indices (all data) | R1 = 0.1533,<br>wR2 = 0.1999 |
| Absorption coefficient | 2.881 mm$^{-1}$ | Largest diff. peak and hole | 0.971 and −0.776 e.Å$^{-3}$ |
| F(000) | 7048 | CIF-ALERTS | B |

Example 55: preparation of (Z)-4-(4-chlorophenyl)-5-(hydroxyimino)-2-phenylcyclopenta-1,3-diene-1-carbonitrile (IV-4)

Brick red solid;
$^1$H NMR (400 MHz, DMSO-d$_6$, δ=2.49 ppm as standard): δ 8.05 (dd, J=6.0, 3.2 Hz, 2H), 7.85 (d, J=8.6 Hz, 2H), 7.65 (s, 1H), 7.60-7.58 (m, 3H), 7.51 (d, J=8.6 Hz, 2H);
$^{13}$C NMR (100 MHz, DMSO-d$_6$, δ=39.5 ppm as standard): δ 159.2 (C), 155.6 (C), 138.8 (C), 133.6 (C), 131.7 (C), 131.5 (C), 131.0 (CH), 130.6 (2×CH), 130.4 (CH), 129.2 (2×CH), 128.5 (2×CH), 128.1 (2×CH), 117.5 (C), 86.1 (C);
HRMS ESI (m/z): calcd for C$_{18}$H$_{12}$C$_1$N$_2$O [M+H]$^+$ 307.0638, found 307.0633.

Example 56: preparation of (Z)-5-(hydroxyimino)-4-(naphthalen-2-yl)-2-phenylcyclopenta-1,3-diene-1-carbonitrile (IV-5)

Brick red solid;
$^1$H NMR (500 MHz, CDCl$_3$, δ=7.24 ppm as standard): δ 8.23 (s, 1H), 8.01 (dd, J=6.5 and 2.5 Hz, 2H), 7.83 (J=ddd, 8.5, 6.5, 2.5 Hz, 3H), 7.74 (dd, J=8.5, 2.0 Hz, 1H), 7.53-7.52 (m, 3H), 7.49 (dd, J=6.25, 3.25 Hz, 2H), 7.21 (s, 1H), n-Hexane grease (1.24, 0.86);
$^{13}$C NMR (125 MHz, CDCl$_3$, δ=77.0 ppm as standard): δ161.0 (C), 157.2 (C), 141.7 (C), 133.4 (C), 133.2 (C), 131.8 (CH), 130.1 (CH), 129.4 (C), 129.24 (C), 129.16 (2×CH), 128.98 (CH), 128.6 (CH), 128.2 (3×CH), 127.7 (CH), 126.9 (CH), 126.5 (CH), 126.0 (CH), 117.7 (C), 87.8 (C), n-Hexane grease (31.9, 29.7, 22.7, 14.1);
HRMS ESI (m/z): calcd for C$_{22}$H$_{15}$N$_2$O [M+H]$^+$ 323.1184, found 323.1175.

Example 57: Preparation of (Z)-5-(hydroxyimino)-2-(3-methoxyphenyl)-4-phenylcyclopenta-1,3-diene-1-carbonitrile (IV-6)

Brick red solid;
$^1$H NMR (400 MHz, CDCl$_3$, δ=7.24 ppm as standard): δ 9.71 (s, OH), 7.66 (d, J=6.8 Hz, 2H), 7.55 (s, 1H), 7.51 (d, J=7.6 Hz, 1H), 7.43-7.34 (m, 4H), 7.07 (m, 2H), 3.88 (s, 3H, OCH$_3$), n-Hexane grease (1.24, 0.86); n-Hexane grease (1.24, 0.86);
$^{13}$C NMR (100 MHz, CDCl$_3$, δ=77.0 ppm as standard): δ 160.8 (C), 160.0 (C), 157.0 (C), 141.8 (C), 133.0 (C), 132.1 (C), 130.1 (CH), 129.9 (CH), 129.1 (CH), 129.0 (2×CH), 128.6 (2×CH), 120.7 (CH), 118.2 (CH), 117.7 (C), 112.8 (CH), 87.7 (C), 55.5 (OCH$_3$), n-Hexane grease (29.7, 22.7, 14.1);
HRMS ESI (m/z): calcd for C$_{19}$H$_{15}$N$_2$O$_2$ [M+H]$^+$ 303.1134, found 303.1133.

Example 58: preparation of (Z)-5-(hydroxyimino)-4-phenyl-2-(4-(trifluoromethyl)phenyl)cyclopenta-1,3-diene-1-carbonitrile (IV-7)

Brick red solid;
$^1$H NMR (500 MHz, CD$_2$Cl$_2$, δ=5.30 ppm as standard): δ9.44 (s, OH), 8.07 (d, J=8.25 Hz, 2H), 7.79 (d, J=8.25 Hz, 2H), 7.69 (dd, J=7.75, 2.0 Hz, 2H), 7.40-7.39 (m, 3H), 7.11 (s, 1H), n-Hexane grease (1.24, 0.86);
$^{13}$C NMR (125 MHz, CDCl$_3$, δ=77.0 ppm as standard): δ 159.9 (C), 157.3 (C), 142.4 (C), 135.7 (C), 132.9 (q, J(C,F)=32.5 Hz, C), 132.2 (C), 130.0 (CH), 129.6 (CH), 129.4 (2×CH), 128.95 (2×CH), 128.88 (2×CH), 126.42 (q, J(C,F)=269.2 Hz, CF$_3$), 126.40 (q, J(CH,F)=3.5 Hz, (2×CH)), 117.1 (C), 89.6 (C), n-Hexane grease (30.1);
HRMS ESI (m/z): calcd for C$_{19}$H$_{12}$F$_3$N$_2$O [M+H]$^+$ 341.0902, found 341.0902.

The results in Table 15 indicate that the disclosed method works reliably for a variety of substitution patterns of the starting material, yielding functionalized cyclopentadienone oximes in high yields and good diastereoselectivity.

The preferred embodiments of the disclosure were described, but the disclosure is not limited to those. It is known to one skilled in the art that some modifications and variations may be made without departing from the spirit and scope of the present disclosure. Hence, the scope of the disclosure should be defined by the following claims.

What is claimed is:
1. A method for producing a cyclic compound, comprising reacting a compound of formula (I) with a compound of formula (II) in presence of a base,

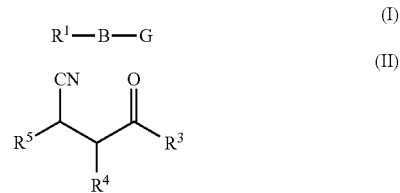

wherein the cyclic compound has an unsaturated five-membered carbon ring formed by the reaction, and
in formula (I),
B is an unsaturated moiety selected from the group consisting of substituted or unsubstituted vinylene, ethynylene, aryleneethynylene, substituted or unsubstituted arylenevinylene, and a combination thereof, wherein the vinylene or arylenevinylene has n substituent(s) R$^2$ independently selected from the group consisting of deuterium, substituted and unsubstituted alkyl, alkenyl, alkynyl, alkenynyl, aryl, alkylaryl, arylalkyl, allyl, benzyl, cycloalkyl, cycloalkenyl, cycloalkynyl, cycloalkenynyl, alkanoyl, aryloyl, alkylsilyl, arylsilyl, alkoxysilyl, aryloxysilyl, alkoxycarbonyl, aryloxycarbonyl, heterocyclic ring, heteroaromatic ring, alkylsulfinyl, arylsulfinyl, alkylsulfonyl, arylsulfonyl, ester derivatives, amide derivatives and metal salt derivatives of phosphonic acid group, phosphinic acid group, boric acid group, carboxylic acid group, sulfinic acid group, sulfonic acid group, sulfamic acid group and amino acid group, aliphatic moieties having a repeating unit of —(OCH$_2$CH$_2$)$_q$OCH$_3$, —(OCH$_2$CH(CH$_3$))$_q$OCH$_3$ —(CH$_2$)$_q$CF$_3$, —(CF$_2$)$_q$CF$_3$ or —(CH$_2$)$_q$CH$_3$, in which q=1, aliphatic chains having a moiety of (OR$^{18}$)$_r$OR$^{19}$, in which R$^{18}$ is a divalent C$_{1-7}$ alkylene moiety, R$^{19}$ is C$_{1-20}$ alkyl and 1≤r≤50, and substituted groups obtained by further substituting the above mentioned substituent groups with ester group, amino acid group, halo, epoxy group, amino, amido, acyl, organosilyl, organotin, organogermyl, nitro, alkoxy, aryloxy, alkyl, aryl, heteroaryl, alkylthio, heteroarylthio, arylthiol, or an ester derivative, an amide derivative or a metal salt derivative of phosphonic acid group, phosphinic acid group, boric acid group, carboxylic acid group, sulfinic acid group, sulfonic acid group, sulfamic acid group or amino acid group, n is 0, 1 or 2, and when n is 2, the two $R^2$ may be the same or different, and may joint together to form a ring;

G is an electron-withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, electron-withdrawing heteroaromatic groups, halogen-substituted alkyl groups, and halogen atoms;

$R^1$ is hydrogen, or deuterium, or a substituent that is less electron-withdrawing than the electron-withdrawing group G, or unsubstituted alkyl, alkenyl, alkynyl, alkenynyl, aryl, alkylaryl, arylalkyl, allyl, benzyl, cycloalkyl, cycloalkenyl, cycloalkynyl, cycloalkenynyl, alkylsilyl, arylsilyl, alkoxysilyl or aryloxysilyl, or a substituent obtained by substituting any of the above unsubstituted groups with epoxy, amino, organosilyl, organotin, organogermyl, alkoxy, aryloxy, alkyl, aryl, heteroaryl, alkylthio, heteroarylthio or arylthio; and two of $R^1$, $R^2$ and G may joint together to form a ring;

in formula (II), each of $R^3$ and $R^4$ is independently hydrogen or a substituent selected from the group from which $R^2$ is selected, wherein $R^3$ and $R^4$ are the same or different;

$R^5$ is an electron-withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, electron-withdrawing heteroaromatic groups, halogen-substituted alkyl groups, and halogen atoms; and two of $R^3$, $R^4$ and $R^5$ may joint together to form a ring; and a conjugate acid of the base has a $pK_a$ in a range of 1 to 15, wherein the base is selected from the group consisting of bases containing carbonate anion, bases containing bicarbonate anion, nitrogen-containing bases, and fluoride containing bases.

2. The method of claim 1, wherein the base comprises a fluoride ion.

3. The method of claim 1, wherein the reaction is carried out in an aprotic solvent.

4. The method of claim 1, wherein the reaction is carried out in a solvent having a dielectric constant of at least 6.

5. The method of claim 1, wherein the reaction is carried out in an anhydrous solvent.

6. The method of claim 1, wherein the reaction is stirred at a temperature comprised in a range of 0° C. to 45° C.

7. A reaction mixture, comprising a compound of formula (I), a compound of formula (II), and a base,

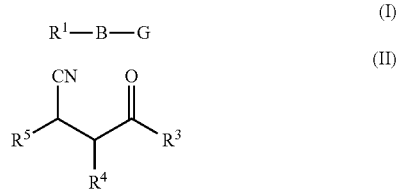

wherein in formula (I),

B is an unsaturated moiety selected from the group consisting of substituted or unsubstituted vinylene, ethynylene, aryleneethynylene, substituted or unsubstituted arylenevinylene, and a combination thereof, wherein the vinylene or arylenevinylene has n substituent(s) $R^2$ independently selected from the group consisting of deuterium, substituted and unsubstituted alkyl, alkenyl, alkynyl, alkenynyl, aryl, alkylaryl, arylalkyl, allyl, benzyl, cycloalkyl, cycloalkenyl, cycloalkynyl, cycloalkenynyl, alkanoyl, aryloyl, alkylsilyl, arylsilyl, alkoxysilyl, aryloxysilyl, alkoxycarbonyl, aryloxycarbonyl, heterocyclic ring, heteroaromatic ring, alkylsulfinyl, arylsulfinyl, alkylsulfonyl, arylsulfonyl, ester derivatives, amide derivatives and metal salt derivatives of phosphonic acid group, phosphinic acid group, boric acid group, carboxylic acid group, sulfinic acid group, sulfonic acid group, sulfamic acid group and amino acid group, aliphatic moieties having a repeating unit of —$(OCH_2CH_2)_q$ $OCH_3$, —$(OCH_2CH(CH_3))_qOCH_3$ —$(CH_2)_qCF_3$, —$(CF_2)_qCF_3$ or —$(CH_2)_qCH_3$, in which q=1, aliphatic chains having a moiety of $(OR^{18})_rOR^{19}$, in which $R^{18}$ is a divalent $C_{1-7}$ alkylene moiety, $R^{19}$ is $C_{1-20}$ alkyl and 1≤r≤50, and substituent groups obtained by further substituting the above mentioned substituent groups with ester group, amino acid group, halo, epoxy group, amino, amido, acyl, organosilyl, organotin, organogermyl, nitro, alkoxy, aryloxy, alkyl, aryl, heteroaryl, alkylthio, heteroarylthio, arylthiol, or an ester derivative, an amide derivative or a metal salt derivative of phosphonic acid group, phosphinic acid group, boric acid group, carboxylic acid group, sulfinic acid group, sulfonic acid group, sulfamic acid group or amino acid group, n is 0, 1 or 2, and when n is 2, the two $R^2$ may be the same or different, and may joint together to form a ring;

G is an electron-withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, electron-withdrawing heteroaromatic groups, halogen-substituted alkyl groups, and halogen atoms;

$R^1$ is hydrogen, or deuterium, or a substituent that is less electron-withdrawing than the electron-withdrawing group G, or unsubstituted alkyl, alkenyl, alkynyl, alkenynyl, aryl, alkylaryl, arylalkyl, allyl, benzyl, cycloalkyl, cycloalkenyl, cycloalkynyl, cycloalkenynyl, alkylsilyl, arylsilyl, alkoxysilyl or aryloxysily, or a substituent obtained by substituting any of the above unsubstituted groups with epoxy, amino, organosilyl, organotin, organogermyl, alkoxy, aryloxy, alkyl, aryl, heteroaryl, alkylthio, heteroarylthio or arylthio; and two of $R^1$, $R^2$ and G may joint together to form a ring;

in formula (II), each of $R^3$ and $R^4$ is independently hydrogen or a substituent selected from the group from which $R^2$ is selected, wherein $R^3$ and $R^4$ are the same or different, and may joint together to form a ring; and $R^5$ is an electron-withdrawing group selected from the group consisting of oxygen-containing electron-withdrawing groups, nitrogen-containing electron-withdrawing groups, sulfur-containing electron-withdrawing groups, phosphorous-containing electron-withdrawing groups, electron-withdrawing aromatic groups, electron-withdrawing heteroaromatic groups, halogen-substituted alkyl groups, and halogen atoms; and a conjugate acid of the base has a $pK_a$ in a range from 1 to 15, wherein the base is selected from the group consisting of bases containing carbonate anion, bases containing bicarbonate anion, nitrogen-containing bases, and fluoride containing bases.

8. The reaction mixture of claim 7, wherein the base comprises a fluoride ion.

9. The reaction mixture of claim 7, further comprising an aprotic solvent.

10. The reaction mixture of claim 7, further comprising a solvent having a dielectric constant of at least 6.

11. The reaction mixture of claim 7, further comprising an anhydrous solvent.

\* \* \* \* \*